(12) United States Patent
Blaszczyk et al.

(10) Patent No.: US 10,329,310 B2
(45) Date of Patent: Jun. 25, 2019

(54) ARGINASE INHIBITORS AND THEIR THERAPEUTIC APPLICATIONS

(71) Applicant: ONCOARENDI THERAPEUTICS S.A., Warsaw (PL)

(72) Inventors: Roman Blaszczyk, Lodz (PL); Joanna Brzezinska, Lodz (PL); Adam A. Golebiowski, Madison, CT (US); Jacek Olczak, Lodz (PL)

(73) Assignee: Onco Arendi Therapeutics S.A., Warsaw (PL)

( * ) Notice: Subject to any disclaimer, the term of this patent is extended or adjusted under 35 U.S.C. 154(b) by 0 days.

(21) Appl. No.: 15/540,888

(22) PCT Filed: Dec. 22, 2015

(86) PCT No.: PCT/PL2015/050073
§ 371 (c)(1),
(2) Date: Jun. 29, 2017

(87) PCT Pub. No.: WO2016/108707
PCT Pub. Date: Jul. 7, 2016

(65) Prior Publication Data
US 2018/0009830 A1 Jan. 11, 2018

Related U.S. Application Data

(60) Provisional application No. 62/097,163, filed on Dec. 29, 2014.

(30) Foreign Application Priority Data

Dec. 29, 2014 (PL) ..................................... P.410665

(51) Int. Cl.
C07D 211/96 (2006.01)
C07F 5/02 (2006.01)
A01N 1/02 (2006.01)

(52) U.S. Cl.
CPC ............ *C07F 5/025* (2013.01); *A01N 1/0226* (2013.01); *C07D 211/96* (2013.01)

(58) Field of Classification Search
CPC ...... C07D 211/96; C07F 5/025; A01N 1/0226
See application file for complete search history.

(56) References Cited

U.S. PATENT DOCUMENTS

| 5,284,656 A | 2/1994 | Platz et al. |
| 5,451,569 A | 9/1995 | Wong et al. |
| 2014/0371175 A1 | 12/2014 | VanZandt et al. |

FOREIGN PATENT DOCUMENTS

| WO | 9919295 A1 | 4/1999 |
| WO | 08061612 A1 | 5/2008 |
| WO | 2010/085797 A2 | 7/2010 |
| WO | 10085797 A2 | 7/2010 |
| WO | 11133653 A1 | 10/2011 |
| WO | 12058065 A1 | 5/2012 |
| WO | 12091757 A1 | 6/2012 |
| WO | 2012/091757 A1 | 7/2012 |
| WO | 13059437 A1 | 4/2013 |
| WO | 13158262 A1 | 10/2013 |

OTHER PUBLICATIONS

The International Search Report (ISR) for PCT/PL2015/050073 dated Feb. 19, 2016, pp. 1-4.
Written Opinion of the International Searching Authority for PCT/PL2015/050073 dated Feb. 19, 2016, pp. 1-5.
International Preliminary Report on Patentability for PCT/PL2015/050073 dated Oct. 28, 2016, pp. 1-14.
Jenkinson, C.P. et al. "Comparative properties of arginases" Comp. Biochem. Physiol., 114B, 1, 107-132, (1996).
Munder, M. "Arginase: an emerging key player in the mammalian immune system" British Journal of Pharmacology, 158, 638-651 (2009).
Rodriguez, P.C. et al. "Regulation of T cell receptor CD3zeta chain expression by L-arginine." J. Biol. Chem., 277, 24, 21123-21129 (2002).
Bronte, V. et al. "IL-4-Induced Arginase 1 Suppresses Alloreactive T Cells in Tumor-Bearing Mice" J. Immunol., 170, 270-278 (2003).
Rodriguez, P.C. et al. "Arginase I production in the tumor microenvironment by mature myeloid cells inhibits T-cell receptor expression and antigen-specific T-cell responses" Cancer Res., 64, 16, 5839-5849 (2004).
Zea, A.H. et al. "Arginase-producing myeloid suppressor cells in renal cell carcinoma patients: a mechanism of tumor evasion" Cancer Res. 65, 8, 3044-3048 (2005).
Bronte, V. et al. "Boosting antitumor responses of T lymphocytes infiltrating human prostate cancers" J. Exp. Med. 201, 8, 1257-1268 2005).
Serafini, P. et al. Phosphodiesterase-5 inhibition augments endogenous antitumor immunity by reducing myeloid-derived suppressor cell function. J Exp Med. 203(12):2691-2702 (2006).
Norian, L. A. et al. "Tumor-infiltrating regulatory dendritic cells inhibit CD8+ T cell function via L-arginine metabolism" Cancer Res. 69, 7, 3086-3094 (2009).
Golebiowski, A. et al. "2-Substituted-2-amino-6-boronohexanoic acids as arginase inhibitors" Bioorg. & Med. Chem. Lett., 23, 2027-2030 (2013).
Oswein, J. Q. et al. "Aerosolization of Proteins" Proceedings of Symposium on Respiratory Drug Delivery II, Keystone, Colorado, p. 1-34 (Mar. 1990).
Newmark, J. et al., "Preparation and Properties of Adducts of Streptokinase and Streptokinase-Plasmin Complex with Polyethylene Glycol and Pluronic Polyol F38" J. Appl. Biochem., 4, 185-189 (1982).
Adjei, A. et al., "Pulmonary Delivery of Peptide Drugs: Effect of Particle Size on Bioavailability of Leuprolide Acetate in Healthy Male Volunteers" Pharm. Res., 7, 6, 565-569 (1990).

(Continued)

*Primary Examiner* — Rebecca L Anderson
(74) *Attorney, Agent, or Firm* — McDonnell Boehnen Hulbert & Berghoff LLP

(57) ABSTRACT

The inventive compounds are small molecule therapeutics that are potent inhibitors of arginase 1 and arginase 2 activity. The inventions also provides pharmaceutical compositions and methods for using the inventive compounds for treating or preventing a disease or condition associated with arginase activity.

36 Claims, No Drawings

(56) References Cited

OTHER PUBLICATIONS

Figure 1:
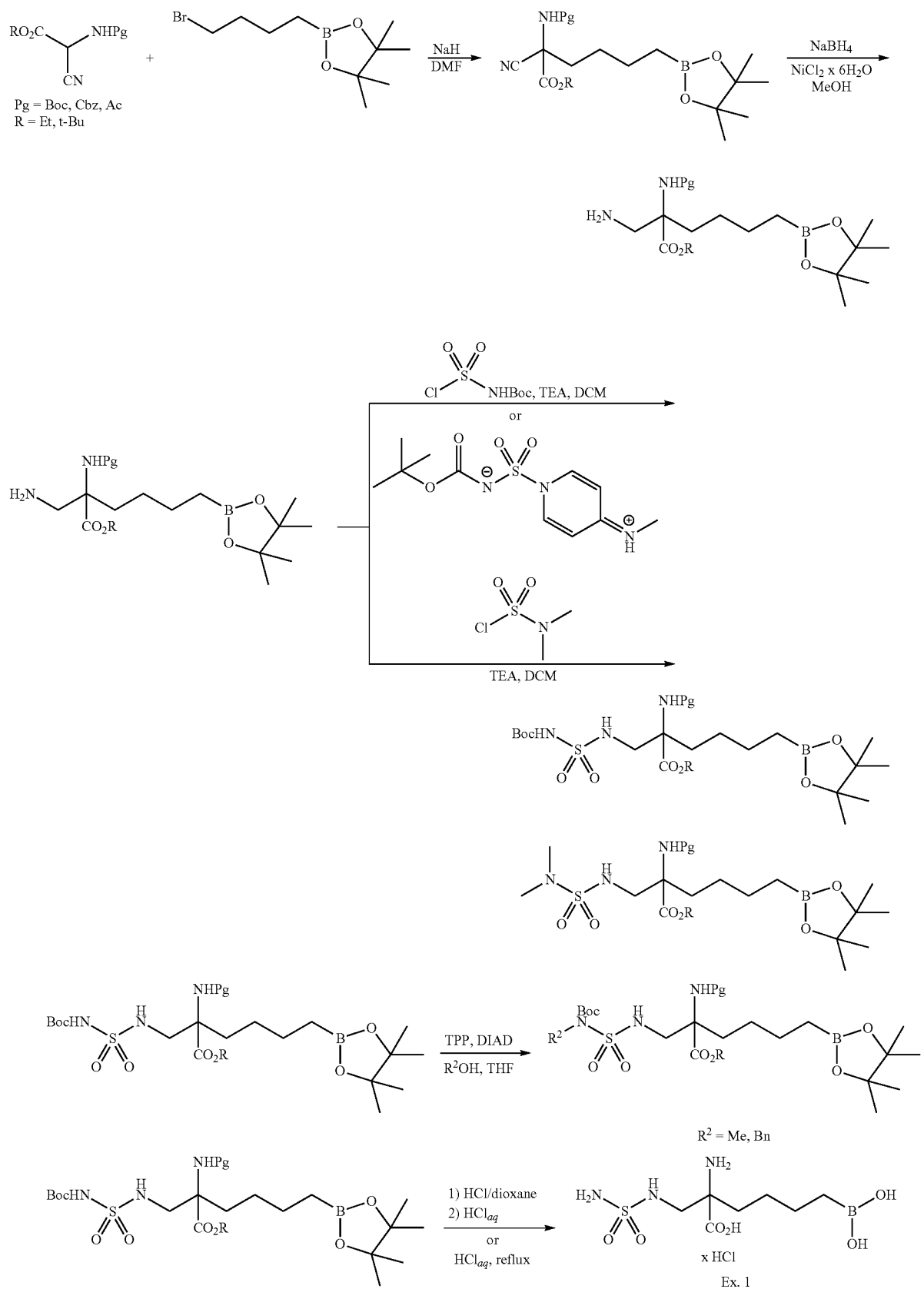

Adjei, A. et al., "Bioavailability of Leuprolide Following Intratracheal Administration to Beagle Dogs" Int. J. Pharmaceutics, 61, 135-144 (1990).
Braquet, P. et al. "Effect of Endothelin-1 on Blood Pressure and Bronchopulmonary System of the Guinea Pig" J. Cardiovasc. Pharmacol., 13(suppl. S), S143-S146 (1989).
Hubbard, R. C. et al., "Anti-Neutrophil-Elastase Defenses of the Lower Respiratory Tract in at-Antitrypsin Deficiency Directly Augmented with an Aerosol of a1-Antitrypsin" Annal. Int. Med. III, 206-212 (1989).
Smith, R. M. et al., "Pulmonary Deposition and Clearance of Aerosolized Alpha-1-Proteinase Inhibitor Administered to dogs and to Sheep" J. Clin. Invest, 84, 1145-1146 (1989).
Debs, R. J. et al., "Lung-specific Delivery of Dytokines Induces Sustained Pulmonary and Systemic Immunodulation in Rats" J. Immunol., 140, 3482-3488 (1988).
Langer, R., "New Methods of Drug Delivery" Science, 249, 1527-33 (1990).
Sawhney, A. S. et al., "Bioerodible Hydrogels Based on Photopolymerized Poly(ethylene glycol)-co-poly(a-hydroxy acid) Diacrylate Macromers" Macromolecules, 26, 581-587 (1993).
Golebiowski, A. et al. "Synthesis of Quaternary A-amino Acid-based Arginase Inhibitors Via the Ugi Reaction" Bioorganic & Medicinal Chemistry Letters, 23, 4837-4841 (2013).
Baggio, R. et al. "Biochemical and Functional Profile of a Newly Developed Potent and Isozyme-Selective Arginase Inhibitor" J. Pharmacol. Exp. Ther., 290, 1409-1416 (1999).

ARGINASE INHIBITORS AND THEIR THERAPEUTIC APPLICATIONS

RELATED APPLICATIONS

This application is a U.S. national phase of International Application No. PCT/PL2015/050073, filed Dec. 22, 2015, which claims priority from Polish application no. P.410665, filed Dec. 29, 2014, and from U.S. Provisional Application No. 62/097,163, filed Dec. 29, 2014, the disclosure of each of which is hereby incorporated by reference in its entirety.

BACKGROUND OF THE INVENTION

The present invention relates generally to inhibitors of arginase and their use for the treatment of pathological states. Two arginase isozymes (ARG-1 and ARG-2, denoted also as arginase I and II, respectively) exist in mammals, that hydrolyze arginine to ornithine and urea. Both enzymes catalyze the same biochemical reaction, but differ in cellular expression level, regulation and subcellular localization. ARG-1 is a cytosolic protein and ARG-2 is mainly localized in mitochondria (Jenkinson C P, Grody W W, Cederbaum S D. Comparative properties of arginases. *Comparative biochemistry and physiology Part B, Biochemistry & Molecular Biology.* 1996; 114(1):107-132).

The arginases are implicated in various pathological states. These include, without limitation, asthma, pulmonary hypertension, hypertension, T cell dysfunction, erectile dysfunction, atherosclerosis, renal disease, ischemia reperfusion injury, neurodegenerative diseases, wound healing, inflammatory diseases, fibrotic diseases and cancer.

Arginase expression and L-arginine depletion is known immune-suppressive pathway of the mammalian immune system (Munder M. Arginase: an emerging key player in the mammalian immune system. *Br J Pharmacol.* 2009; 158(3): 638-651). L-arginine deficiency down-regulates expression of T cell receptor (TCR) ζ chain, a key signaling element of the TCR, thereby impairing T cell function (Rodriguez P C, Zea A H, Culotta K S, Zabaleta J, Ochoa J B, Ochoa A C. Regulation of T cell receptor CD3zeta chain expression by L-arginine. *J Biol Chem.* 2002; 277(24):21123-21129). Depletion of L-arginine from the microenvironment leads to an arrest in T cell cycle progression, inhibition of IFN-γ production, and blocking of signaling through the T cell receptor.

Arginases are mainly produced by myeloid-derived suppressor cells (MDSC) that are highly enriched in the tumor-bearing state (Bronte V, Serafini P, De Santo C, Mariango I, Tosello V, Mazzoni A, Segal D M, Staib C, Lowel M, Sutter G, Colombo M P, Zanovello P: IL-4-Induced Arginase 1 Suppresses Alloreactive T Cells in Tumor-Bearing Mice *J Immunol* 2003; 170:270-278). Induction of arginase pathway is an important mechanisms involved in the evasion of anti-tumor immunity. High arginase activity has been observed in patients with various malignancies, both in blood and within tumor mass.

It was shown that T cell functions are restored and tumor growth is inhibited upon inhibition of arginase of tumor-associated MDSC or tumor-infiltrating CD11b$^+$Gr-1$^-$ mature myeloid cells in various murine tumor models (Rodriguez P C, Quiceno D G, Zabaleta J, et al. Arginase I production in the tumor microenvironment by mature myeloid cells inhibits T-cell receptor expression and antigen-specific T-cell responses. *Cancer Res.* 2004; 64(16): 5839-5849). Depletion of the myeloid suppressor cells re-establishes T cell receptor- and costimulation-induced T cell activation (Zea A H, Rodriguez P C, Atkins M B, et al. Arginase-producing myeloid suppressor cells in renal cell carcinoma patients: a mechanism of tumor evasion. *Cancer Res.* 2005; 65(8):3044-3048).

Arginase was shown to participate in the suppression of tumor-infiltrating lymphocytes in patients with prostate carcinoma (Bronte V, Kasic T, Gri G, et al. Boosting antitumor responses of T lymphocytes infiltrating human prostate cancers. *J Exp Med.* 2005; 201(8):1257-1268), non-small cell lung carcinoma (Rodriguez P C, Quiceno D G, Zabaleta J, et al. Arginase I production in the tumor microenvironment by mature myeloid cells inhibits T-cell receptor expression and antigen-specific T-cell responses. *Cancer Res.* 2004; 64(16):5839-5849) and multiple myeloma (Serafini P, Meckel K, Kelso M, et al. Phosphodiesterase-5 inhibition augments endogenous antitumor immunity by reducing myeloid-derived suppressor cell function. *J Exp Med.* 2006; 203(12):2691-2702). Not only MDSC but also dendritic cells (DCs) have been shown to suppress CD8$^+$ T cells and antitumor immune responses through ARG-1 production (Norian L A, Rodriguez P C, O'Mara L A, et al. Tumor-infiltrating regulatory dendritic cells inhibit CD8+ T cell function via L-arginine metabolism. *Cancer Res.* 2009; 69(7):3086-3094).

Given the role of arginase in various pathological states and their role in chronic inflammation and suppression of anti-tumor immunity, the present invention provides novel boron-containing compounds as inhibitors of arginase activity, as well as methodologies for using these compounds as therapeutics.

Numerous boron-containing arginase inhibitors are well-known from the literature. One of such inhibitors is 2(S)-amino-6-boronohexanoic acid, as described in WO9919295A1, published on Apr. 22, 1999, and in WO08061612A1, published on May 29, 2008. Besides, WO11133653, published on Oct. 27, 2011, and WO13059437, published on Apr. 25, 2013, describe a number of alpha-amino acid derivatives bearing a terminal B(OH)$_2$ group and a spacer, usually being a 1,3-cyclobutylene moiety. Mono- or polycyclic boron-containing amino acid compounds suitable as arginase inhibitors are described in WO12058065, published on May 3, 2012. Another related patent application publications are WO10085797 of Jul. 29, 2010, WO13158262 of Oct. 24, 2013, and WO12091757 of Jun. 5, 2012.

Significance of substitution at the alpha center of 2-amino-6-boronohecanoic acid for the inhibitory potency of arginase I and arginase II inhibitors has been discussed (Golebiowski A., et al. 2-Substituted-2-amino-6-borono-hexanoic acids as arginase inhibitors. *Bioorg. & Med. Chem. Lett.,* 2013; 23:2027-2030).

There is a need to investigate the inhibition of arginases, and to discover treatments for conditions associated with elevated expression of arginases, such as asthma and allergic responses. In particular, there is a need to explore new molecular scaffolds that effectively inhibit arginases and, therefore, can act as therapeutic agents for the treatment of these conditions.

The present inventors arrived at small molecule arginase inhibitors that proved to be very active, and exhibited superior pharmacokinetics.

SUMMARY OF THE INVENTION

In one aspect, the invention provides a compound represented by formula (I), or a stereoisomer, a tautomer, a pharmaceutically acceptable salt, or a solvate thereof:

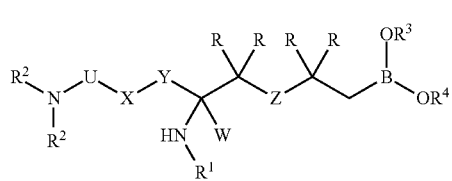

(I)

wherein:

U is —C(R)₂—, —C(=O)—, —C(=NH)—, —S(O)—, or —S(O)₂—;

W is —CO₂H, —C(O)O((C₁-C₆)alkyl), —C(O)NHOH, —C(O)NHCN, —C(O)NH₂, —C(O)NH((C₁-C₆)alkyl), —C(O)N((C₁-C₆)alkyl)₂, —C(O)NH(aryl), —C(O)N(aryl)((C₁-C₆)alkyl), —C(O)N(aryl)₂, —C(O)NH((C₁-C₆)haloalkyl), —S(O)₂NH₂, —S(O)₂NH((C₁-C₆)alkyl), —S(O)₂NH((C₁-C₆)haloalkyl), —S(O)₂NH(aryl), —S(O)₂NHC(O)((C₁-C₆)alkyl), —S(O)₂NHC(O)((C₁-C₆)haloalkyl), —S(O)₂NHC(O)(aryl), —N(H)S(O)₂((C₁-C₆)alkyl), —N(H)S(O)₂(aryl), N(H)S(O)₂((C₁-C₆)haloalkyl), —NHC(O)((C₁-C₆)alkyl), —NHC(O)((C₁-C₆)haloalkyl), —NHC(O)(aryl), —NHC(O)NH((C₁-C₆)alkyl), —NHC(O)NH(aryl), —C(O)N(H)S(O)₂((C₁-C₆)alkyl), —C(O)N(H)S(O)₂(aryl), —C(O)N(H)S(O)₂((C₁-C₆)haloalkyl), —P(O)(OH)₂, —CF₃

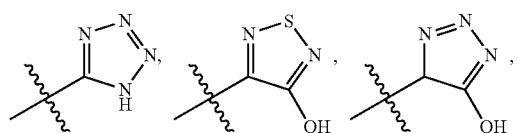

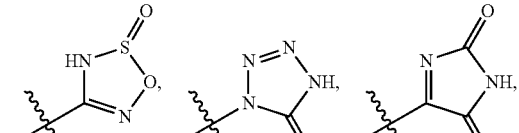

Q = CH₂, NH, S, O   Q = CH₂, NH, S, O

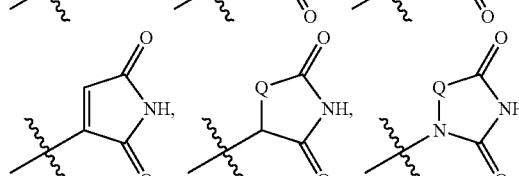

R' = (C₁-C₆)alkyl

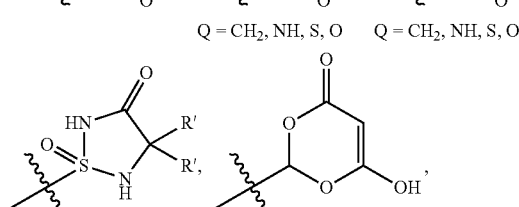

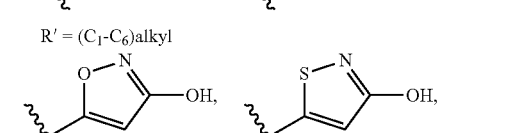

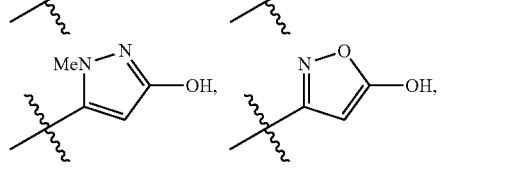

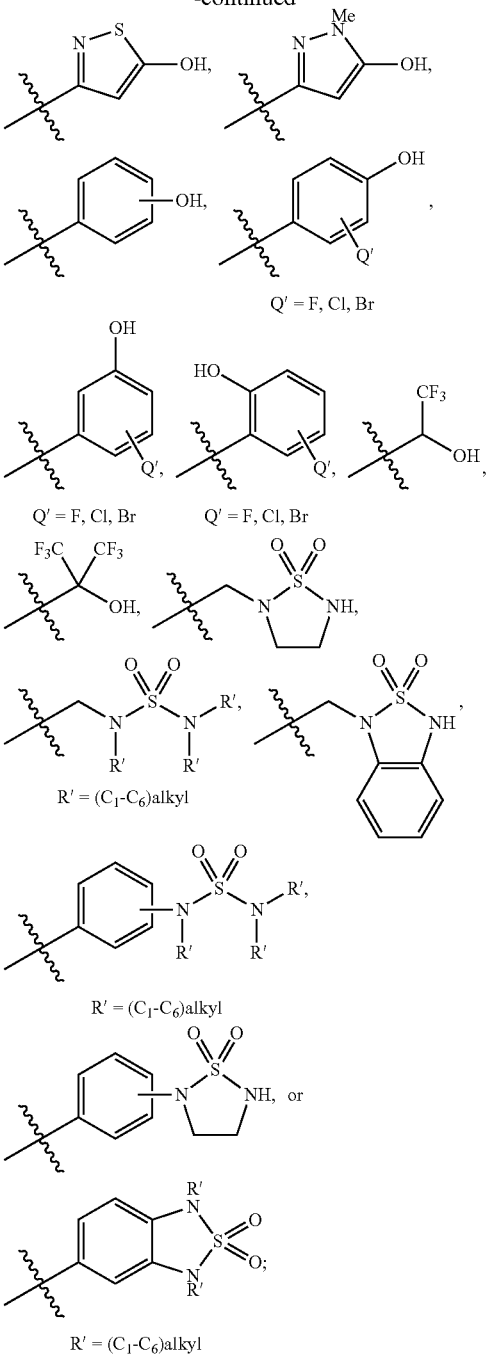

X is —NR¹ or —C(R)₂—;

Y is —(C₁-C₃)alkylene- optionally substituted by one or more R substituents;

Z is —C(R)₂—, —O—, —S—, —SO—, or —SO₂—;

each R independently is selected from —H, —(C₁-C₃)alkyl, -halo, or —OH;

R¹ is —H or —SO₂NH₂ or —(C₁-C₃)alkyl;

each R² independently is selected from H, alkyl, aryl, arylalkyl, heteroaryl, heteroarylalkyl, heterocyclyl, or heterocyclylalkyl;

R³ and R⁴ are each independently selected from hydrogen, straight or branched (C₁-C₆)alkyl, and C(O)—R', or R³ and R⁴ together with the boron atom to which they are bound via oxygen atoms form a 4-, 5-, 6-, or 7-membered ring that is fully saturated, or partially saturated;

if X=—NH—, Y=—CH₂—, and the R substituent located three bonds apart to Y is CH₃, then one H atom at X and one H atom at R may be replaced with a bond, thus forming a 5-membered pyrrolidinyl ring, and optionally if W comprises CO₂H group then it may form a cyclic moiety resulting from condensation with —NHSO₂NH₂.

Example compounds of the Formula (I) according to the invention include those of the following structural formulae:

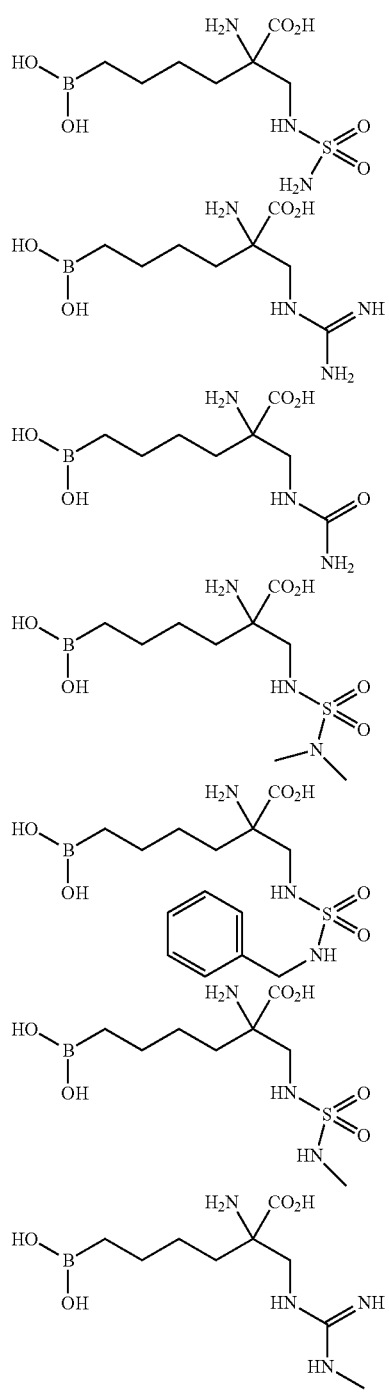

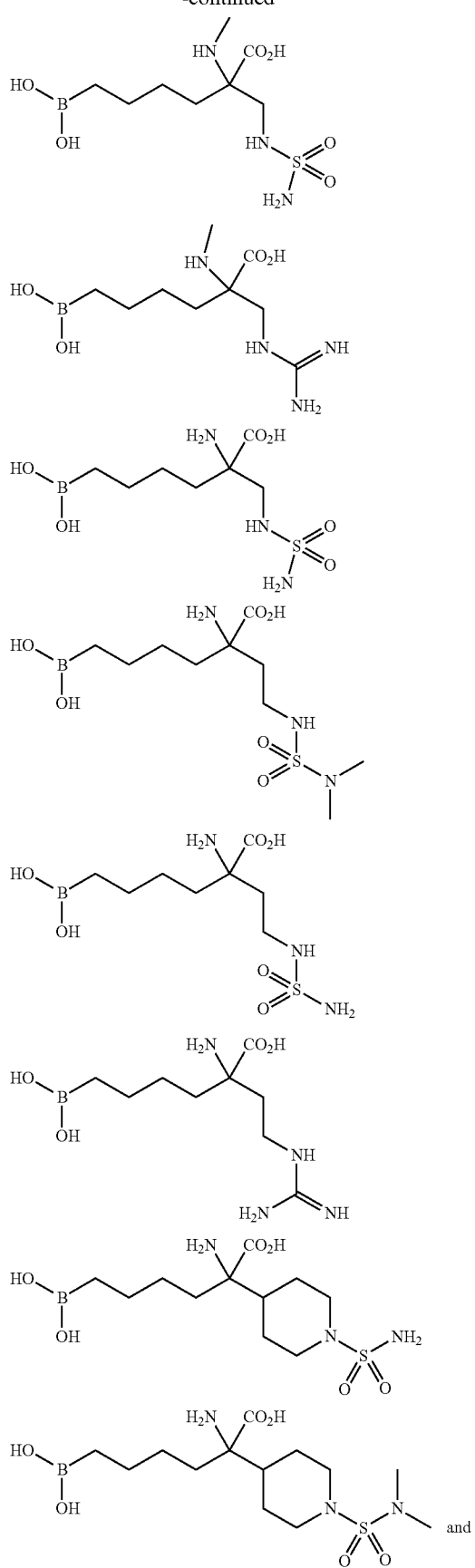

-continued

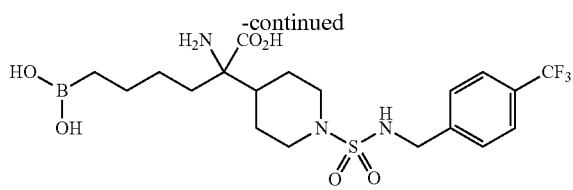

In a particularly preferred embodiment, the invention relates to a compound selected from:
2-amino-6-borono-2-((sulfamoylamino)methyl)hexanoic acid,
2-amino-6-borono-2-(guanidinomethyl)hexanoic acid, and
6-borono-2-(guanidinomethyl)-2-(methylamino)hexanoic acid,
and/or stereoisomers, tautomers, pharmaceutically acceptable salts, and/or solvates thereof.

Also provided herein are pharmaceutical compositions, comprising (i) a therapeutically effective amount of at least one compound of the invention, or a stereoisomer, tautomer, pharmaceutically acceptable salt, solvate, or prodrug thereof; and (ii) a pharmaceutically acceptable carrier.

In another aspect, the invention provides a method for inhibiting arginase I, arginase II, or a combination thereof in a cell, comprising contacting the cell with at least one compound according to the invention, or a stereoisomer, tautomer, pharmaceutically acceptable salt, solvate, or prodrug thereof.

In another aspect, the invention provides a method for the treatment or prevention of a disease or condition associated with expression or activity of arginase I, arginase II, or a combination thereof in a subject, comprising administering to the subject therapeutically effective amount of at least one compound according to the invention, or a stereoisomer, tautomer, pharmaceutically acceptable salt, solvate, or prodrug thereof.

In another aspect, the invention provides use of a compound according to the invention, or a stereoisomer, tautomer, pharmaceutically acceptable salt, solvate, or prodrug thereof in the manufacture of a medicament for the treatment or prevention of a disease or condition associated with expression or activity of arginase I, arginase II, or a combination thereof.

In another aspect, the invention provides use of a compound according to the invention, or a stereoisomer, tautomer, pharmaceutically acceptable salt, solvate, or prodrug thereof, for providing organ protection during transport.

DETAILED DESCRIPTION

The present invention is based on a surprising finding that some small molecule arginase inhibitors possess very high activity accompanied by superior pharmacokinetics.

Definitions

The articles "a" and "an" are used herein to refer to one or to more than one (i.e., to at least one) of the grammatical object of the article. By way of example, "an element" means one element or more than one element.

The terms used herein may be preceded and/or followed by a single dash "—", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, $(C_1-C_6)$-alkoxycarbonyloxy and —OC(O)$(C_1-C_6)$alkyl indicate the same functionality; similarly arylalkyl and -alkylaryl indicate the same functionality.

The term "heteroatom" is art-recognized and refers to an atom of any element other than carbon or hydrogen. Illustrative heteroatoms include boron, nitrogen, oxygen, phosphorus, sulfur and selenium.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1-C_{30}$ for straight chain, $C_3-C_{30}$ for branched chain), and alternatively, about 20 or fewer, 10 or fewer, or preferably 1-6 carbons. Representative examples of alkyl include, but are not limited to, methyl, ethyl, n-propyl, isopropyl, n-butyl, sec-butyl, isobutyl, tert-butyl, n-pentyl, isopentyl, neopentyl, and n-hexyl.

The term "cycloalkyl" means mono- or bicyclic or bridged saturated or partially saturated carbocyclic rings, each having from 3 to 12 carbon atoms. Certain cycloalkyls have from 3-8, or from 3-6 carbon atoms in their ring structure. Certain cycloalkyls have from 5-12 carbon atoms in their ring structure, and may have 6-10 carbons in the ring structure. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "heterocyclyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 14, or 3 to 12 atoms including at least one heteroatom, such as nitrogen, oxygen, or sulfur. More preferred heterocycloalkyl groups have from 5-10 ring members where from 1-4 of the ring members are hetero atoms selected from the group consisting of O, N, and S, the remaining ring atoms being C. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinicludinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group is optionally substituted by one or more substituents as described below.

As used herein, the term "heterocyclylene" refers to a bivalent heterocyclyl (heterocycloalkyl) group, i.e., a cyclic alkylene group, having from 3-10 members and from 1-4 hetero atoms selected from S, O, and N. An example is piperidine-2,3-dicarboxylic acid, i.e., in that compound, the piperidine ring is a heterocyclyl group.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "cycloalkylalkyl" as used herein refers to an alkyl group substituted with one or more cycloalkyl groups.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

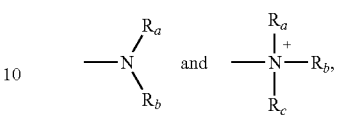

wherein $R_a$, $R_b$, and $R_c$ each independently represent a hydrogen, an alkyl, an alkenyl, $-(CH_2)_x-R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally Re) each independently represent a hydrogen, an alkyl, an alkenyl, or $-(CH_2)_x-R_d$. In certain embodiments, the term "amino" refers to $-NH_2$.

The term "amido", as used herein, means $-NHC(=O)-$, wherein the amido group is bound to the parent molecular moiety through the nitrogen. Examples of amido include alkylamido such as $CH_3C(=O)N(H)-$ and $CH_3CH_2C(=O)N(H)-$.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

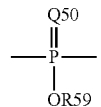

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

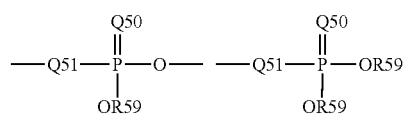

wherein Q50 and R59, each independently, are defined above, and Q51 represents O, S or N; for example, —O—P (O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an —N$_3$ group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—.

The term "carboxy", as used herein, means a —CO$_2$H group.

The term "aryl" is a term of art and as used herein refers to includes monocyclic, bicyclic and polycyclic aromatic hydrocarbon groups, for example, benzene, naphthalene, anthracene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. Representative examples of the polcyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to a phenyl group.

The term "heteroaryl" is a term of art and as used herein refers to a monocyclic, bicyclic, and polycyclic aromatic group having 3 to 14, 5 to 14, or 3 to 12 total atoms including one or more heteroatoms such as nitrogen, oxygen, or sulfur in the ring structure. More preferred heteroaryl groups have from 5-10 ring members where from 1-4 of the ring members are hetero atoms selected from the group consisting of O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Any heteroaryl or bicyclic heteroaryl can be optionally substituted as detailed below.

The term "aralkyl", "arylalkyl", or "aryl(C$_1$-C$_6$)alkyl" is a term of art and as used herein refers to an alkyl group, for example a C$_1$-C$_6$ alkyl group, substituted with an aryl group, wherein the moiety is appended to the parent molecule through the alkyl group.

The term "heteroaralkyl", "heteroarylalkyl", or "heteroaryl(C$_1$-C$_6$)alkyl" is a term of art and as used herein refers to an alkyl group, for example a C$_1$-C$_6$ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH—CH_2—O—$) and vinyloxy (i.e., $CH_2=CH—O—$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The terms "cyano" and "nitrile" is a term of art and as used herein refers to —CN.

The term "nitro", as used herein, means —$NO_2$.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms. The term "haloalkoxyl" refers to an alkoxy group, as defined herein, wherein some or all of the hydrogens are replaced with halogen atoms. An exemplary haloalkyl group is trifluoromethyl.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si—$) group (i.e., (hydrocarbyl)$_3Si—$), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or other substitutents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T.W.; Wuts, P.G.M. *Protective Groups in Organic Synthesis,* 2$^{nd}$ ed.; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

A "unsaturated" or "partially saturated" compound means that the referenced chemical structure may contains on or more multiple carbon-carbon bonds, but is not aromatic. For example, a unsaturated cycloalkyl group as defined herein includes cyclohexenyl, cyclopentenyl, cyclohexadienyl, and the like.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, pamoic (embonic), succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

As used herein, a protic solvent is a solvent that has a hydrogen atom bound to an oxygen (as in a hydroxyl group) or a nitrogen (as in an amine group). In general terms, any solvent that contains labile H$^+$ is called a protic solvent. The molecules of such solvents readily donate protons (H$^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, "subject" refers to a warm blooded animal such as a mammal, preferably a human, or a human child, which is afflicted with, or has the potential to be afflicted with one or more diseases and disorders described herein.

"EC$_{50}$" refers to a dosage, concentration or amount of a particular test compound that elicits a dose-dependent response at 50% of maximal expression of a particular response that is induced, provoked or potentiated by the particular test compound.

"IC$_{50}$" refers to an amount, concentration or dosage of a particular test compound that achieves a 50% inhibition of a maximal response in an assay that measures such response.

COMPOUNDS OF THE INVENTION

In one aspect, the invention provides a compound represented by Formula (I), or a stereoisomer, a tautomer, a pharmaceutically acceptable salt, or a solvate thereof:

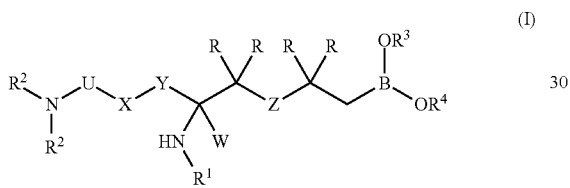

(I)

wherein:
U is —C(R)$_2$—, —C(=O)—, —C(=NH)—, —S(O)—, or —S(O)$_2$—;
W is —CO$_2$H, —C(O)O((C$_1$-C$_6$)alkyl), —C(O)NHOH, —C(O)NHCN, —C(O)NH$_2$, —C(O)NH((C$_1$-C$_6$)alkyl), —C(O)N((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)((C$_1$-C$_6$)alkyl), —S(O)$_2$NHC(O)((C$_1$-C$_6$)haloalkyl), —S(O)$_2$NHC(O)(aryl), —N(H)S(O)$_2$((C$_1$-C$_6$)alkyl), —N(H)S(O)$_2$(aryl), N(H)S(O)$_2$((C$_1$-C$_6$)haloalkyl), —NHC(O)((C$_1$-C$_6$)alkyl), —NHC(O)((C$_1$-C$_6$)haloalkyl), —NHC(O)(aryl), —NHC(O)NH((C$_1$-C$_6$)alkyl), —NHC(O)NH(aryl), —C(O)N(H)S(O)$_2$((C$_1$-C$_6$)alkyl), —C(O)N(H)S(O)$_2$(aryl), —C(O)N(H)S(O)$_2$((C$_1$-C$_6$)haloalkyl), —P(O)(OH)$_2$, —CF$_3$

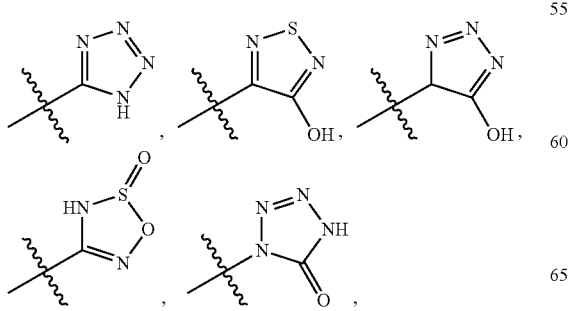

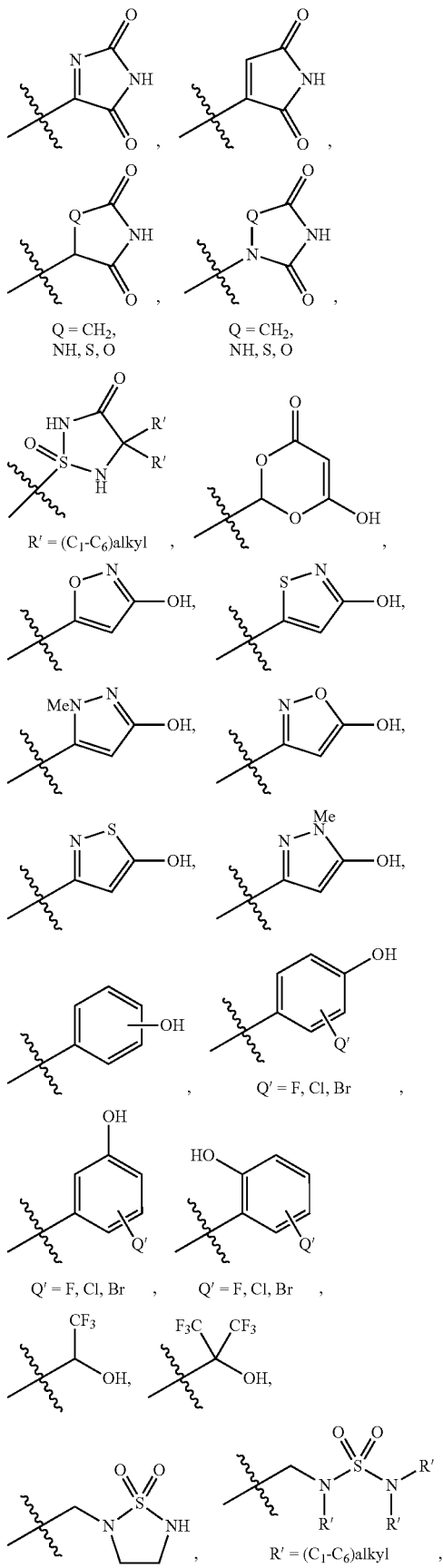

X is $NR^1$ or $-C(R)_2-$;
Y is $-(C_1-C_3)$alkylene- optionally substituted by one or more R substituents;
Z is $-C(R)_2-$, $-O-$, $-S-$, $-SO-$, or $-SO_2-$;
each R independently is selected from $-H$, $-(C_1-C_3)$alkyl, -halo, or $-OH$;
$R^1$ is $-H$ or $-SO_2NH_2$ or $-(C_1-C_3)$alkyl;
each $R^2$ independently is selected from H, alkyl, aryl, arylalkyl, heteroaryl, heteroarylalkyl, heterocyclyl, and heterocyclylalkyl;
$R^3$ and $R^4$ are each independently selected from hydrogen, straight or branched $(C_1-C_6)$alkyl, and C(O)—R',
or $R^3$ and $R^4$ together with the boron atom to which they are bound via oxygen atoms form a 4-, 5-, 6- or 7-membered ring that is fully saturated, or partially saturated;
if X=—NH—, Y=—CH$_2$—, and the R substituent located three bonds apart to Y is CH$_3$, then one H atom at X and one H atom at R may be replaced with a bond, thus forming a 5-membered pyrrolidinyl ring and optionally
if W comprises CO$_2$H group then it may form a cyclic moiety resulting from condensation with —NHSO$_2$NH$_2$.

The above-defined general Formula (I) covers some preferred compounds of the invention, which can be described in more detail as follows.

In certain embodiments, U is —C(=O)—, —C(=NH)—, or —S(O)$_2$—.
In certain embodiments, each R is H.
In certain embodiments, $R^1$ is H or CH$_3$.
In certain embodiments, one of $R^2$ is H and the other is CH$_3$ or benzyl or para-(trifluoromethyl)benzyl.
In certain embodiments, each $R^2$ is H.
In certain embodiments, each $R^2$ is CH$_3$.
In certain embodiments, $R^3$ is H.
In certain embodiments, $R^4$ is H.
In certain embodiments, W is —CO$_2$H or —C(O)NHOH.
In certain embodiments, X is —NH— or —CH$_2$—.
In certain embodiments, Y is —CH$_2$— or —CH$_2$CH$_2$—.

In certain embodiments, the group X—Y denotes piperidinyl-4-yl.
In certain embodiments, Z is —CH$_2$—.
In certain embodiments, the compounds of the Formula (I) according to the invention are in racemic form.
In certain embodiments, the compounds of the Formula (I) according to the invention are the L-enantiomers at the amino acid moiety.
In other embodiments, the compounds of the Formula (I) according to the invention are the D-enantiomers at the amino acid moiety.
Usually, the L-enantiomers are more active biologically than the D-enantiomers.

Example compounds of the Formula (I) according to the invention include those of the following structural formulae:

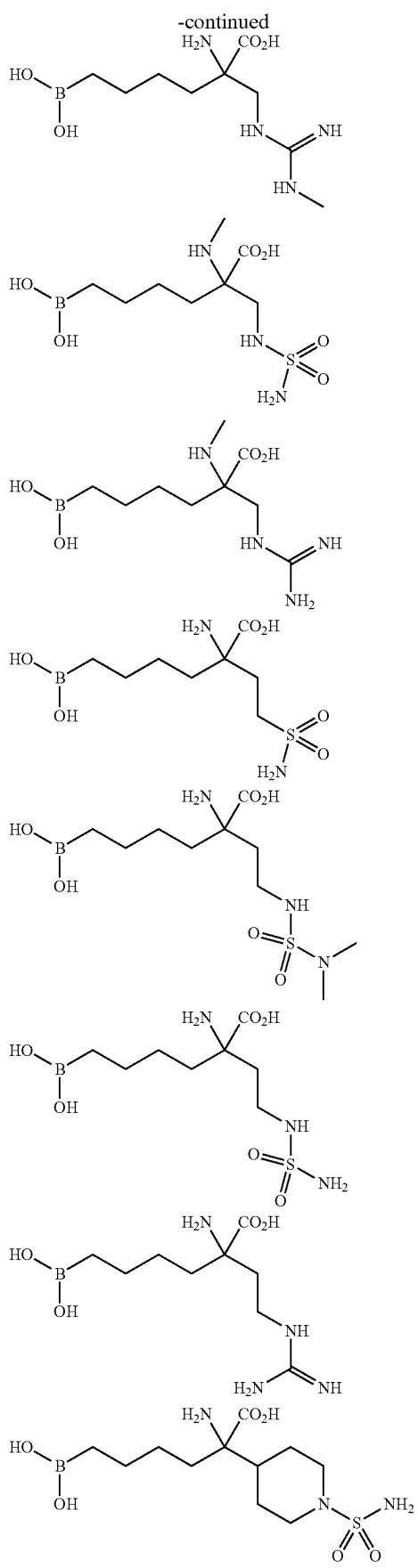

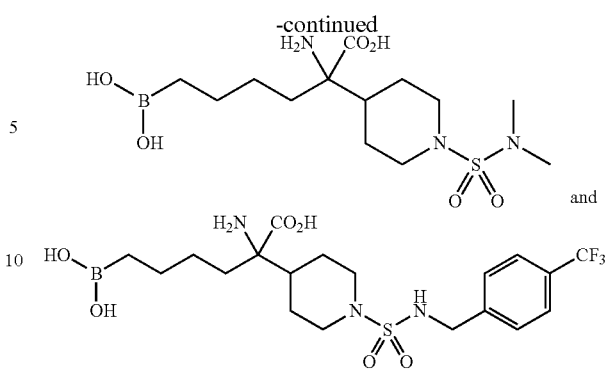

In a particularly preferred embodiment, the invention relates to a compound selected from:
2-amino-6-borono-2-((sulfamoylamino)methyl)hexanoic acid,
2-amino-6-borono-2-(guanidinomethyl)hexanoic acid, and
6-borono-2-(guanidinomethyl)-2-(methylamino)hexanoic acid, and/or a stereoisomer, a tautomer, a pharmaceutically acceptable salt, and/or a solvate thereof.

Pharmaceutical Compositions of the Invention

Also provided herein are pharmaceutical compositions, comprising (i) a therapeutically effective amount of at least one compound of the invention, or a stereoisomer, tautomer, pharmaceutically acceptable salt, solvate, or prodrug thereof; and (ii) a pharmaceutically acceptable carrier.

The exact nature of the carrier, or, for example excipient or diluent, will depend upon the desired use for the composition, and may be suitable or acceptable for veterinary use and/or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, rituxan, PD4 inhibitors, p38 inhibitors, PDE4 inhibitors, and antihistamines.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 20 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5): 143-146 (1989) (endothelin-1); Hubbard et al., *Annal Int Med* 3:206-212 (1989) ($\alpha$1-antitrypsin); Smith et al., 1989, *J Clin Invest* 84:1145-1146 (a-1-proteinase); Oswein et al., 1990, *"Aerosolization of Proteins"*, Proceedings of Symposium on Respiratory Drug Delivery II, Keystone, Colo., March, (recombinant human growth hormone); Debs et al., 1988, *J Immunol* 140:3482-3488 (interferongamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers ($\mu$m), most preferably 0.5 to 5 $\mu$m, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas, e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Methods of the Invention

Another aspect of the invention is a method for treating asthma, comprising administering to a subject in need thereof a therapeutically effective amount of a compound of the invention, for example a compound of any one of formula (I).

In another aspect, the invention provides a method for inhibiting arginase I, arginase II, or a combination thereof in a cell, comprising contacting the cell with at least one compound according to the invention, or a stereoisomer, tautomer, pharmaceutically acceptable salt, solvate, or prodrug thereof.

In another aspect, the invention provides a method for the treatment or prevention of a disease or condition associated with expression or activity of arginase I, arginase II, or a combination thereof in a subject, comprising administering to the subject therapeutically effective amount of at least one compound according to the invention, or a stereoisomer, tautomer, pharmaceutically acceptable salt, solvate, or prodrug thereof.

In certain embodiments, the disease or condition is selected from the group consisting of cardiovascular disorders, sexual disorders, wound healing disorders, gastrointestinal disorders, autoimmune disorders, immune disorders, infections, pulmonary disorders, hemolytic disorders, and cancers.

In certain embodiments, the disease or condition is cardiovascular disorder selected from the group consisting of systemic hypertension, pulmonary arterial hypertension (PAH), pulmonary arterial hypertension in high altitude, ischemia reperfusion (IR) injury, myocardial infarction, atherosclerosis.

In certain embodiments, the disease or condition is pulmonary arterial hypertension (PAH).

In certain embodiments, the disease or condition is myocardial infarction or atherosclerosis.

In certain embodiments, the disease or condition is a pulmonary disorder selected from the group consisting of chemically-induced lung fibrosis, idiopathic pulmonary fibrosis, cystic fibrosis, chronic obstructive pulmonary disease (COPD), and asthma.

In certain embodiments, the disease or condition is an autoimmune disorder selected from the group consisting of selected from the group consisting of encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

In certain embodiments, the disease or condition is an immune disorder selected from the group consisting of myeloid-derived suppressor cell (MDSC) mediated T-cell dysfunction, human immunodeficiency virus (HIV), autoimmune encephalomyelitis, and ABO mismatch transfusion reaction.

In certain embodiments, the disease or condition is myeloid-derived suppressor cell (MDSC) mediated T-cell dysfunction, In certain embodiments, the disease or condition is a hemolytic disorder selected from the group consisting of selected from the group consisting of sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

In certain embodiments, the disease or condition is a gastrointestinal disorder selected from the group consisting of gastrointestinal motility disorders, gastric cancers, inflammatory bowel disease, Crohn's disease, ulcerative colitis, and gastric ulcers.

In certain embodiments, the disease or condition is a sexual disorder selected from the group consisting of Peyronie's disease and erectile dysfunction.

In certain embodiments, the disease or condition is ischemia reperfusion (IR) injury selected from the group consisting of selected from the group consisting of liver IR, kidney IR, and myocardial IR.

In certain embodiments, the disease or condition is a cancer selected from the group consisting of gastric, colon, breast, and lung cancers, including non-small cell lung carcinoma), renal cell carcinoma, prostate carcinoma, multiple myeloma, acute myeloid leukemia, neuroblastoma, glioblastoma, and melanoma.

In certain embodiments, the disease or condition is selected from the group consisting of renal disease inflammation, psoriasis, leishmaniasis, neurodegenerative diseases, wound healing, human immunodeficiency virus (HIV), hepatitis B virus (HBV), *Helicobacter pylori* infections, fibrotic disorders, arthritis, candidiasis, periodontal disease, keloids, adenotonsilar disease, African sleeping sickness and Chagas' disease.

In certain embodiments, the disease or condition is a wound healing disorder selected from the group consisting of infected and uninfected wound healing.

In certain embodiments, the subject is a mammal selected from the group consisting of human, dog, cat, horse, cow, pig, sheep, goat, and ape.

Uses

In another aspect, the invention provides use of a compound according to the invention, or a stereoisomer, tautomer, pharmaceutically acceptable salt, solvate, or prodrug thereof in the manufacture of a medicament for the treatment or prevention of a disease or condition associated with expression or activity of arginase I, arginase II, or a combination thereof.

In another aspect, the invention provides use of a compound according to the invention, or a stereoisomer, tautomer, pharmaceutically acceptable salt, solvate, or prodrug thereof, for providing organ protection during transport.

EXAMPLES

The present invention is further illustrated by the following examples, which in no way should be construed as limiting the scope of the claimed invention.

Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

For the more specific guidance concerning the synthetic approach to boron bearing alpha-amino acids, the reader is referred to the international patent application publications WO11133653 and WO13059437.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "*Protective Groups in Organic Chemistry*," Plenum Press, London and New York 1973, in T. W. Greene and P. G. M. Wuts, "*Protective Groups in Organic Synthesis*," Third edition, Wiley, New York 1999, in "*The Peptides*;" Volume 3 (editors: E. Gross and J. Meienhofer), Academic Press, London and New York 1981, in "*Methoden der organischen Chemie*," Houben-Weyl, 4th edition, Vol. 15/1, Georg Thieme Verlag, Stuttgart 1974, in H.-D. Jakubke and H. Jescheit, "*Aminosauren, Peptide, Proteine*," Verlag Chemie, Weinheim, Deerfield Beach, and Basel 1982, and/or in Jochen Lehmann, "*Chemie der Kohlenhydrate: Monosaccharide und Derivate*," Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Starting materials can be obtained from commercial sources or prepared by well-established literature methods known to those skilled in the art.

All solvents, substrates and reagents that were commercially available were used without further purification. TLC analysis was performed using pre-coated glass plates (0.2±0.03 mm thickness, GF-254, particle size 0.01-0.04 mm) from Fluorochem Ltd, UK. Column chromatography was performed using high-purity grade silica gel (pore size 60 Å, 220-440 mesh particle size, 35-75 μm particle size) from Fluka.

$^1$H and $^{13}$C NMR spectra were recorded on Bruker AVANCE NMR spectrometers at 500 MHz (DRX500), 600 MHz (DRX600), or 700 MHz (DRX700).

$^{19}$F NMR spectra were recorded on a 200 MHz AVANCE Bruker NMR spectrometer.

All spectra were recorded in appropriate deuterated solvents ($CDCl_3$, DMSO-$d_6$, $D_2O$, $CD_3OD$, etc.) that were commercially available.

Resonances are given in parts per million relative to tetramethylsilane. Data are reported as follows: chemical shift, multiplicity (s=singlet, d=doublet, t=triplet, m=multiplet, bs=broad singlet), coupling constants (Hz) and integration.

ESI-MS spectra were obtained on a Waters Alliance 2695 separation module with a PDA 1996 UV detector and Waters Micromass ZQ 2000 mass detector equipped with Kinetex 2.1/50 mm, 2.6 μm C18 column eluted with 0.3 mL/min flow of 3-100% gradient (over 6 min) of acetonitrile in water.

Figure 3:
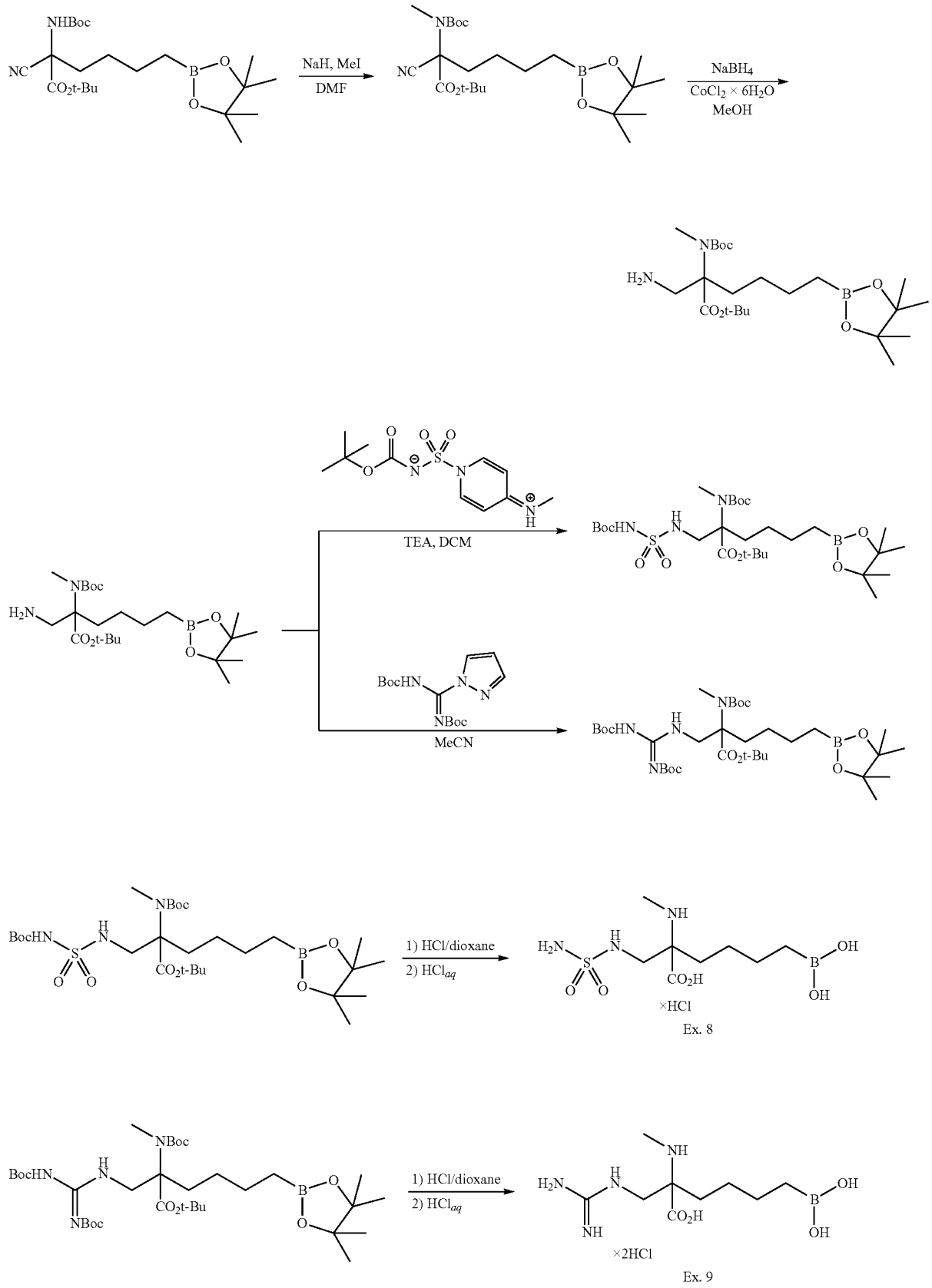
Figure 4:
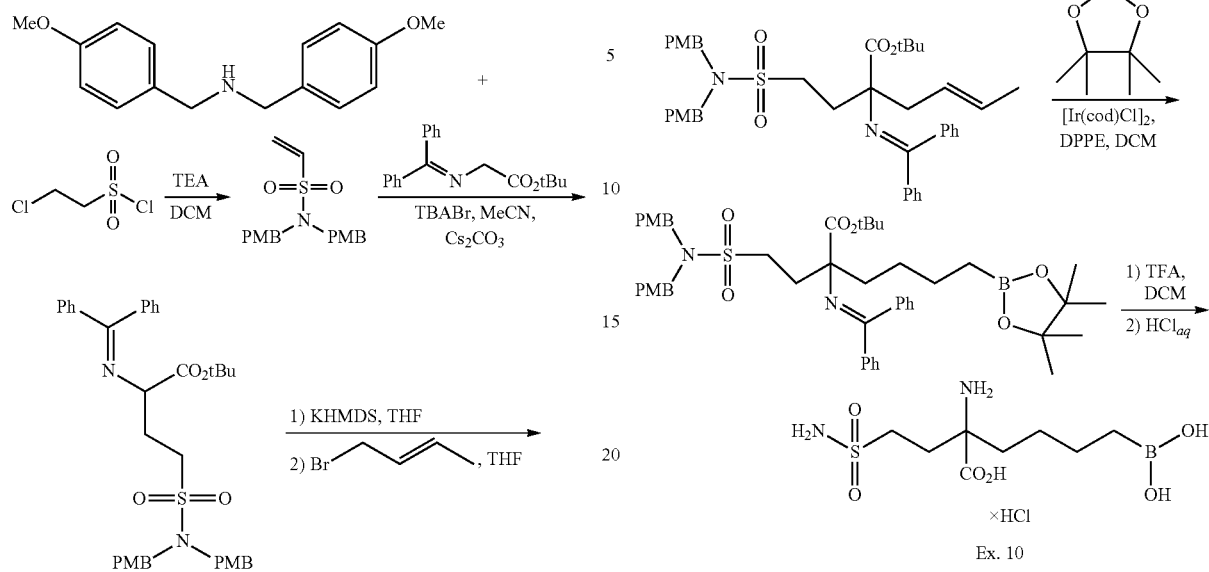
Figure 5:
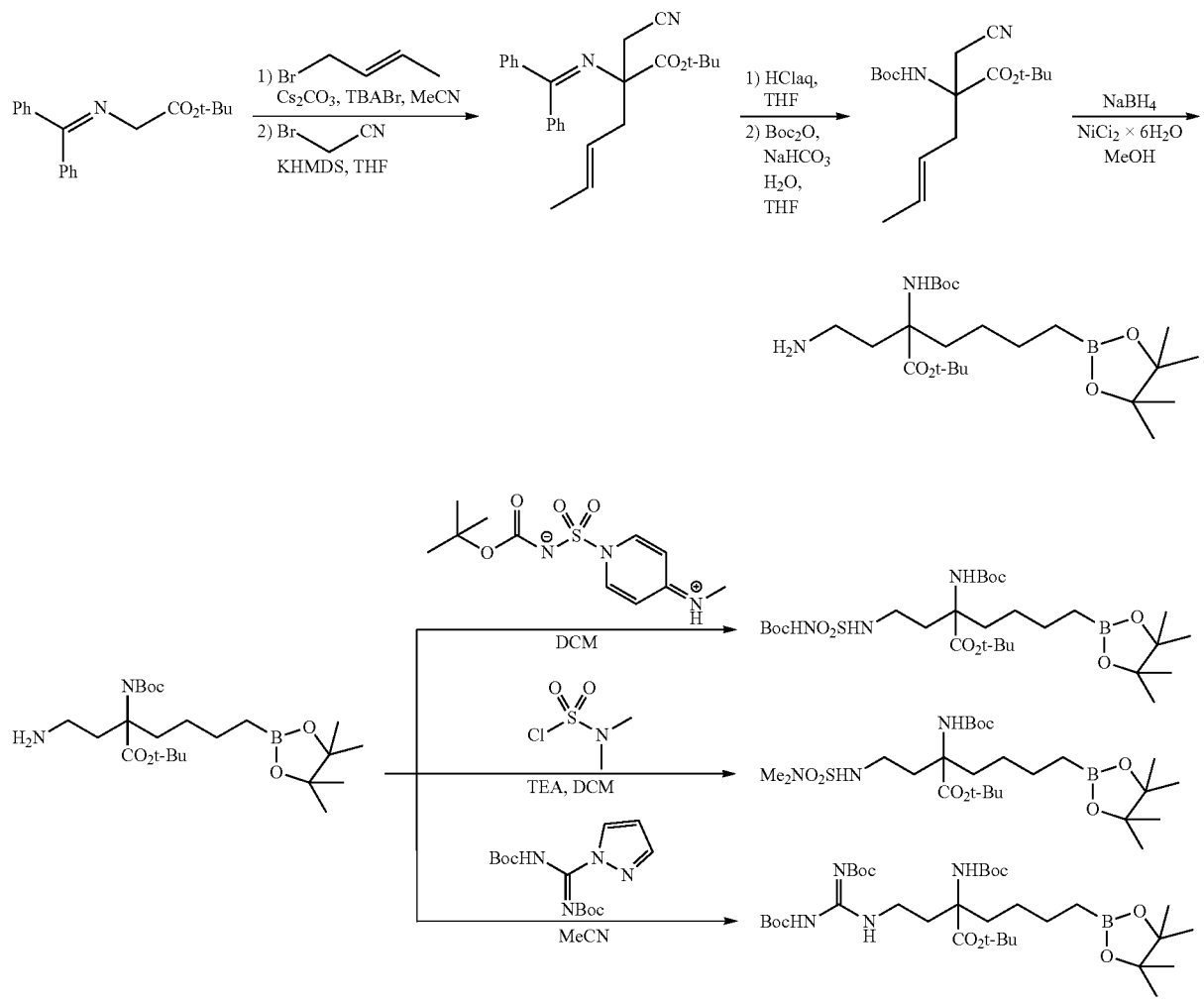

Exemplary general synthetic methodologies for making compounds of Formula (I) are provided below (FIGS. 1-6).

37 38
-continued
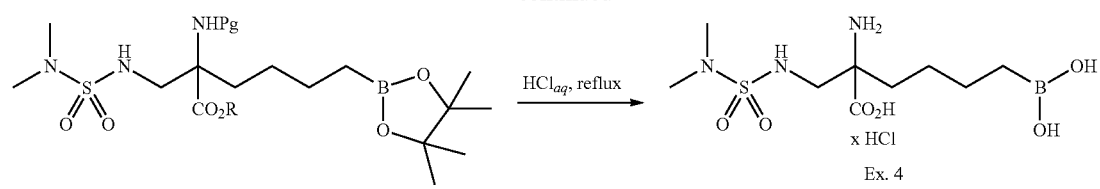
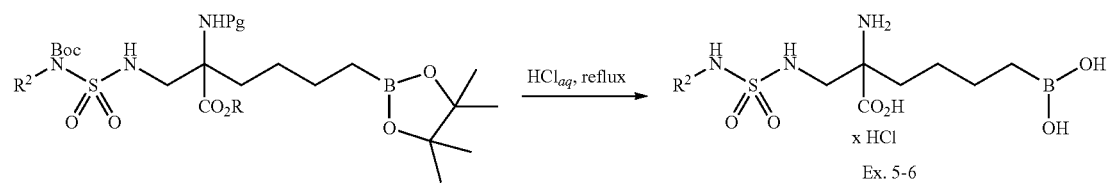
FIG. 2.
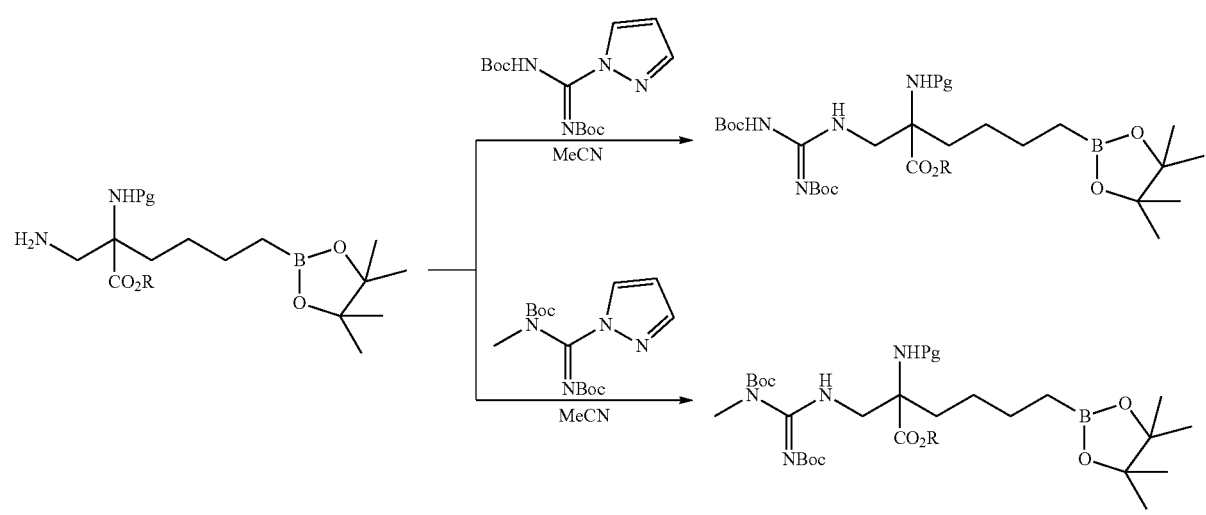
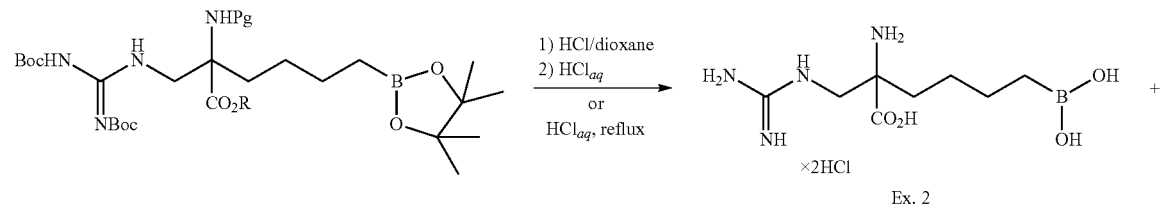
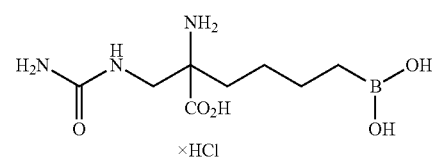
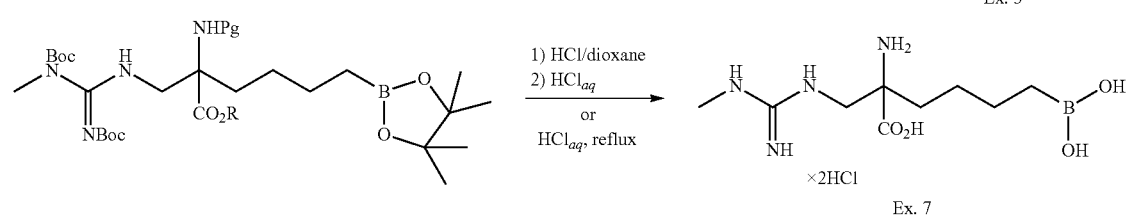

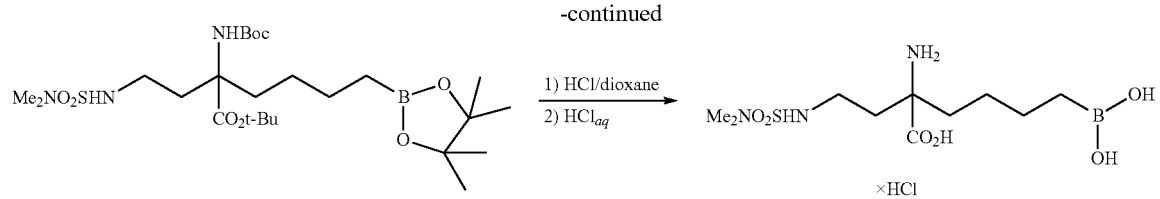
Ex. 11
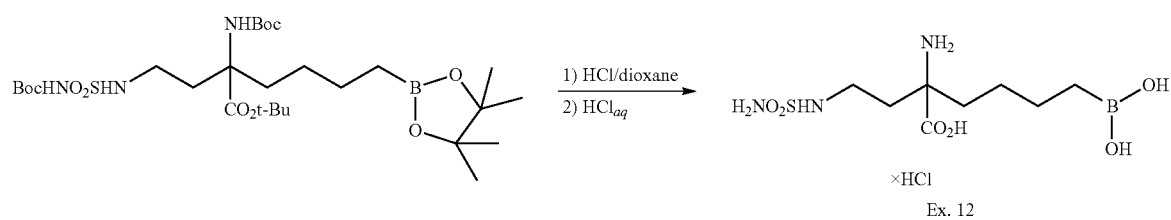
Ex. 12
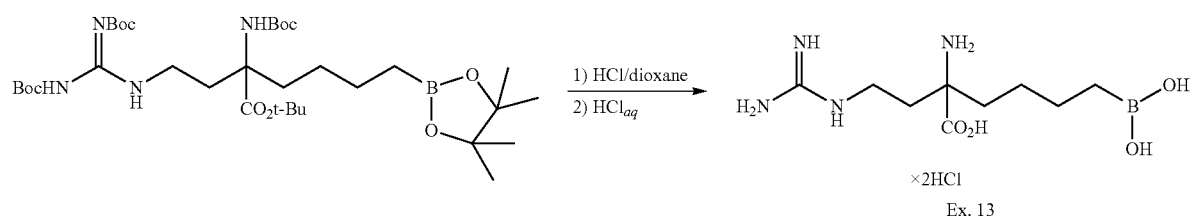
Ex. 13
FIG. 6.
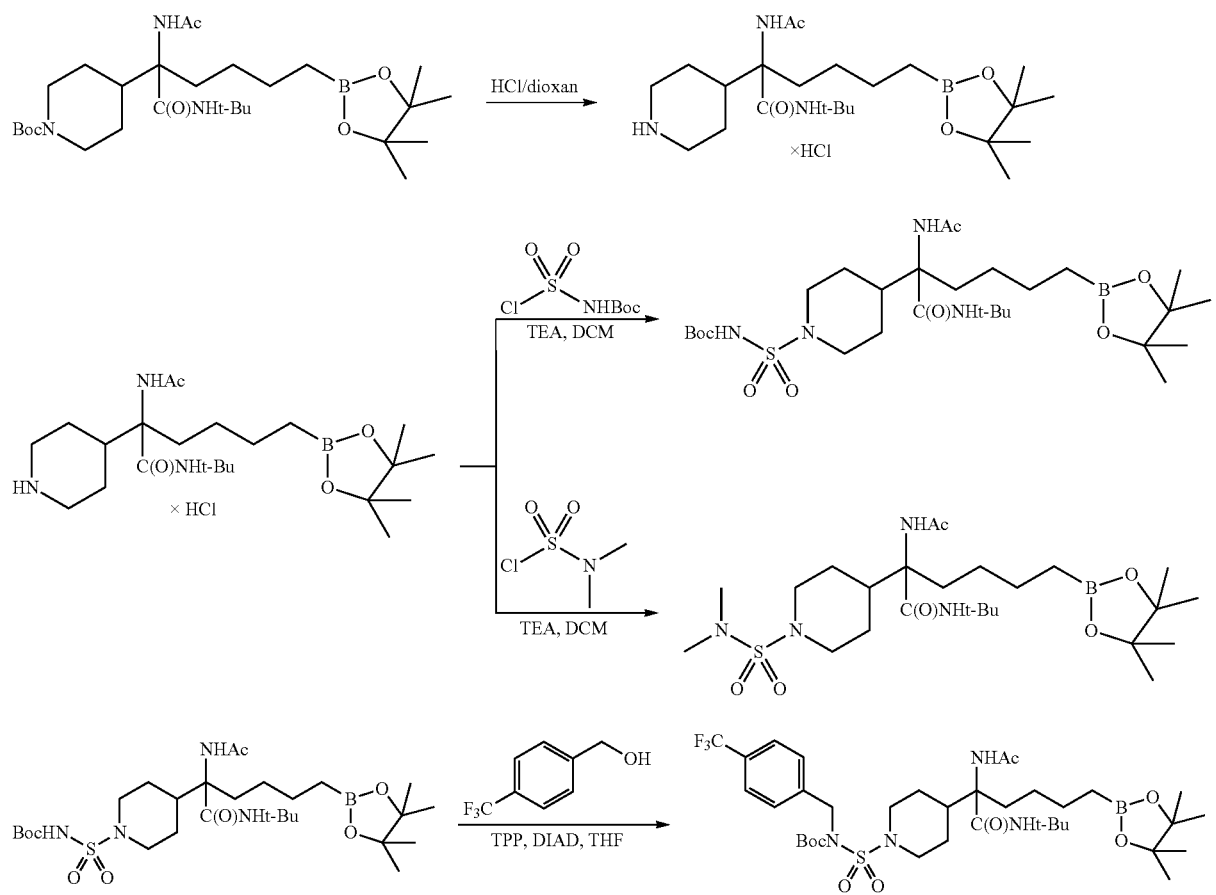

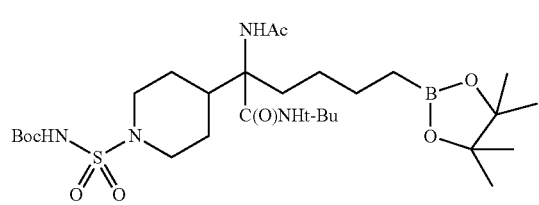 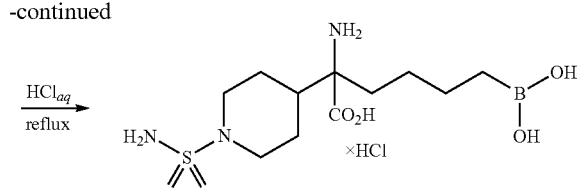

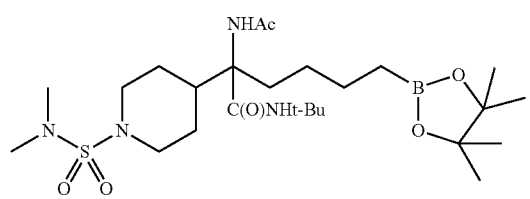 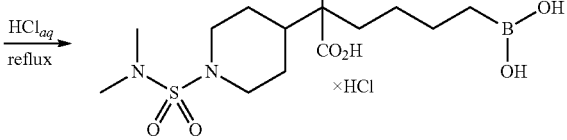

Ex. 14

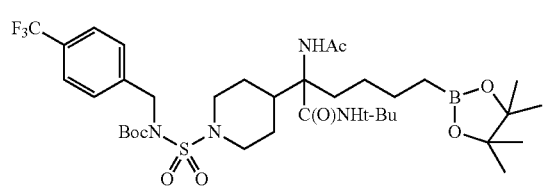 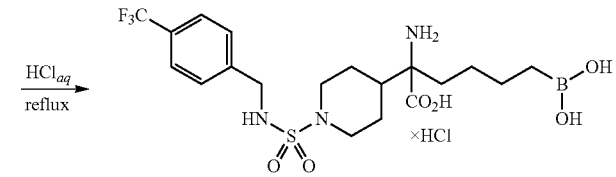

Ex. 15

Ex. 16

Example 1. 2-Amino-6-borono-2-((sulfamoylamino)methyl)hexanoic acid hydrochloride

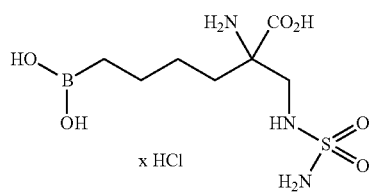

Method A

Step A. Ethyl 2-acetamido-2-(((N-(tert-butoxycarbonyl)sulfamoyl)amino)methyl)-6-(4,4,5,5-tetramethyl-1,3,2-dioxaborolan-2-yl)hexanoate

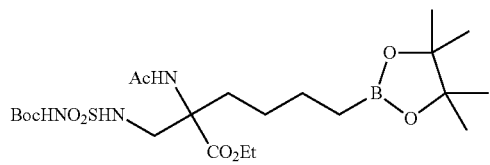

To a solution of chlorosulfonyl isocyanate (0.22 mL, 2.55 mmol) in dichloromethane (2.5 mL) was added tert-butanol (0.24 mL, 2.55 mmol) in dichloromethane (0.6 mL) dropwise at 0° C. The resulting solution was stirred at room temperature for 1 hour to provide tert-butyl (chloro-sulfonyl)carbamate. The solution of tert-butyl (chlorosulfonyl) carbamate (prepared as above) was added dropwise to a solution of ethyl 2-acetamido-2-(aminomethyl)-6-(4,4,5,5-tetramethyl-1,3,2-dioxaborolan-2-yl)hexanoate hydrochloride (1.0 g, 2.55 mmol) (Bioorganic & Medicinal Chemistry Letters 2013, 23, 2027-2030) in dichloromethane (12 mL) at 0° C. After stirring for 5 min, triethylamine (1.14 mL, 8.16 mmol) was added dropwise at 0° C. The reaction was allowed to warm to 10° C. for 0.5 h and then stirred at room temperature for 1.5 h. The reaction mixture was diluted with dichloromethane (70 mL), washed with 1 M $KHSO_4$ (aq) (10 mL), water (10 mL) and 5% $NaHCO_3$(aq) (10 mL) and dried over $MgSO_4$, filtered and concentrated in vacuo to afford a crude product. The crude product was purified by flash column chromatography, on silica gel (hexane/AcOEt 2:1 to 1:1) to give ethyl 2-acetamido-2-(((N-(tert-butoxycarbonyl)-sulfamoyl)amino)methyl)-6-(4,4,5,5-tetramethyl-1,3,2-dioxaborolan-2-yl)hexanoate (0.61 g, 45%) as a white solid. ESI+MS: m/z=536.2 $(M+H)^+$, 558.2 $(M+Na)^+$, ESI-MS: m/z=534.5 $(M-1)^-$. $^1$H NMR (500 MHz, DMSO) δ 10.84 (s, 1H), 7.84 (s, 1H), 7.36 (bdd, J=7.3, 6.3 Hz, 1H), 4.03-3.92 (m, 2H), 3.42 (dd, J=13.5, 5.7 Hz, 1H), 3.18 (dd, J=13.5, 7.9 Hz, 1H), 1.73 (s, 3H), 1.71-1.62 (m, 1H), 1.48 (m, 1H), 1.39 (s, 9H), 1.29-1.15 (m, 4H), 1.15-1.09 (m, 12H), 1.09 (t, J=7.1 Hz, 3H), 0.97-0.75 (m, 2H), 0.58 (t, J=7.2 Hz, 2H).

Step B. 2-Amino-6-borono-2-((sulfamoylamino)methyl)hexanoic acid hydrochloride A mixture of ethyl 2-acetamido-2-(((N-(tert-butoxycarbonyl)sulfamoyl)amino)methyl)-6-(4,4,5,5-tetramethyl-1,3,2-dioxaborolan-2-yl)hexanoate (200 mg, 0.373 mmol), methanol (0.2 mL) and 2 N HCl (2 mL) was heated under reflux for 2.5 h. After cooling to room temperature the reaction mixture was concentrated in vacuo and the residue was purified by preparative HPLC (0.1-10% MeCN in water) to give 2-amino-6-borono-2-((sulfamoylamino)methyl)-hexanoic acid hydrochloride (22 mg, 18%) as a colorless glass. ESI+MS: m/z=284.2 $(M+H)^+$, 266.2 $(M-18+H)^+$, ESI-MS: m/z=282.3 $(M-1)^-$, 264.4 $(M-18-1)^-$. $^1$H NMR (500 MHz, $D_2O$) δ 3.40 (d, J=14.8 Hz, 1H), 3.20 (d, J=14.8

Hz, 1H), 1.77-1.65 (m, 1H), 1.64-1.55 (m, 1H), 1.32-1.16 (m, 3H), 1.15-1.03 (m, 1H), 0.63 (t, J=7.3 Hz, 2H).

Method B

Step A. tert-Butyl 2-((tert-butoxycarbonyl)amino)-2-cyano-6-(4,4,5,5-tetramethyl-1,3,2-dioxaborolan-2-yl)hexanoate

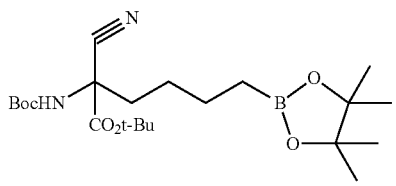 [SMILES: CC(C)(C)OC(=O)NC(C#N)(CCCCB1OC(C)(C)C(C)(C)O1)C(=O)OC(C)(C)C]

To a solution of tert-butyl 2-((tert-butoxycarbonyl) amino)-2-cyanoacetate (92.08 g; 0.0081 mol) in DMF (20 mL) was added sodium hydride (60% in mineral oil; 0.36 g; 0.0089 mol) at 5° C. The resulting mixture was stirred at 5° C. for 15 min. followed by 2-(4-bromobutyl)-4,4,5,5-tetramethyl-1,3,2-dioxaborolane was added drop-wise. The reaction mixture was stirred at room temperature overnight, washed with ethyl acetate (100 mL). The organic layer was separated and washed with water (100 mL) and brine (2×100 mL), dried over MgSO$_4$, filtered and concentrated in vacuo to afford a crude product. The crude material was purified by flash column chromatography, on silica gel (hexane/AcOEt 40:1 to 10:1) to give 1.80 g (51%) of the desired product as a white solid. ESI+MS: m/z=461.2 (M+Na)$^+$. $^1$H NMR (700 MHz, DMSO) δ 8.20 (s, 1H), 1.93-1.73 (m, 2H), 1.49-1.46 (m, 2H), 1.42 (s, 18H), 1.38-1.25 (m, 2H), 1.18 (s, 12H), 0.68 (t, J=7.4 Hz, 2H).

Step B. tert-Butyl 2-(aminomethyl)-2-((tert-butoxycarbonyl)amino)-6-(4,4,5,5-tetramethyl-1,3,2-dioxa-borolan-2-yl)hexanoate

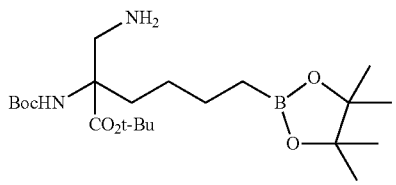 [SMILES: CC(C)(C)OC(=O)NC(CN)(CCCCB1OC(C)(C)C(C)(C)O1)C(=O)OC(C)(C)C]

To a solution of tert-butyl 2-((tert-butoxycarbonyl) amino)-2-cyano-6-(4,4,5,5-tetramethyl-1,3,2-dioxaborolan-2-yl)hexanoate (0.80 g; 0.00182 mol) and NiCl$_2$×6H$_2$O (43 mg; 0.182 mmol) in methanol (12 mL) sodium borohydride (0.48 g; 0.0128 mol) was added portion-wise at 0° C. After stirring for 15 min at room temperature additional amount of NaBH$_4$ (0.48 g; 0.0128 mol) was added portion-wise and stirring was continued for further 15 min. Then the reaction mixture was quenched wit saturated aqueous solution of NH$_4$Cl (50 mL) and filtered through the Celite. The filtrate was then washed with ethyl acetate (4×40 mL). The combined organic layers were washed with brine (20 mL), dried over MgSO$_4$, filtered and concentrated in vacuo to afford 0.70 g of a crude product. The crude product was used to the next step without any further purification. ESI+MS: m/z=443.2 (M+H)$^+$.

Step C. tert-Butyl 2-((tert-butoxycarbonyl)amino)-2-(((N-(tert-butoxycarbonyl)sulfamoyl)-amino) methyl)-6-(4,4,5,5-tetramethyl-1,3,2-dioxaborolan-2-yl)hexanoate

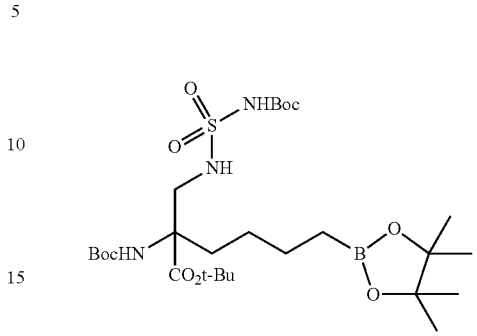

The title compound was prepared in an analogous manner to example 1 (step A) starting from tert-butyl 2-(aminomethyl)-2-((tert-butoxycarbonyl)amino)-6-(4,4,5,5-tetramethyl-1,3,2-dioxa-borolan-2-yl)hexanoate (0.70 g). The crude product was purified by flash column chromatography, on silica gel (hexane/AcOEt 40:1 to 10:1) to give 0.27 g (24% after two steps) of the desired product as a white solid. ESI+MS: m/z=644.1 (M+Na)$^+$. $^1$H NMR (700 MHz, CDCl$_3$) δ 7.11 (bs, 1H), 5.44 (bs, 2H), 3.71 (bd, J=8.9 Hz, 1H), 3.45 (dd, J=12.3, 9.0 Hz, 1H), 2.09-2.18 (m, 1H), 1.68-1.63 (m, 1H), 1.50 (s, 9H), 1.49 (s, 9H), 1.44 (s, 9H), 1.42-1.37 (m, 2H), 1.30-1.27 (m, 1H), 1.24 (s, 12H), 1.18-1.10 (m, 1H), 0.77 (dd, J=8.6, 7.2 Hz, 2H).

Step D. 2-Amino-6-borono-2-((sulfamoylamino) methyl)hexanoic acid hydrochloride tert-Butyl 2-(aminomethyl)-2-((tert-butoxycarbonyl) amino)-6-(4,4,5,5-tetramethyl-1,3,2-dioxa-borolan-2-yl) hexanoate (0.27 g; 0.43 mmol) was treated with 4 M HCl in dioxane (15 mL). The mixture was stirred for 1 hour followed by 6 M HCl (aq) (5 mL) was added and stirring was continued overnight. Dioxane was removed under reduced pressure ant the residue was washed with diethyl ether (20 mL) and concentrated in vacuo. The residue was purified by preparative HPLC (0.1-10% MeCN in water) to give 2-amino-6-borono-2-((sulfamoylamino)methyl)-hexanoic acid hydrochloride (61 mg, 44%) as a white crystalline solid. ESI+MS: m/z=266.1 (M−18+H)$^+$, ESI-MS: m/z=282.4 (M−1)$^-$, 264.4 (M−18−1)$^-$. $^1$H NMR (700 MHz, D$_2$O) δ 3.53 (d, J=14.9 Hz, 1H), 3.31 (d, J=14.9 Hz, 1H), 1.78-1.85 (m, 1H), 1.69-1.74 (m, 1H), 1.37-1.26 (m, 3H), 1.22-1.09 (m, 1H), 0.74-0.62 (m, 2H).

Example 2.
2-Amino-6-borono-2-(guanidinomethyl)hexanoic acid dihydrochloride

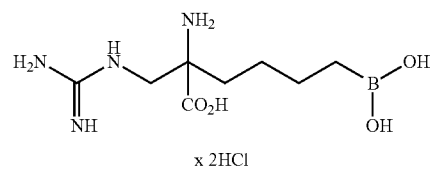 [SMILES: N=C(N)NCC(N)(CCCCB(O)O)C(=O)O]

Step A. Ethyl 2-acetamido-2-((2,3-bis(tert-butoxycarbonyl)guanidino)methyl)-6-(4,4,5,5-tetramethyl-1,3,2-dioxaborolan-2-yl)hexanoate

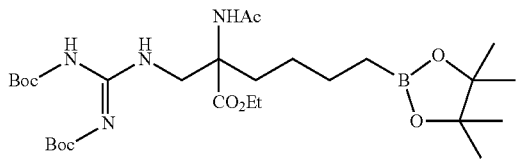 [SMILES: CCOC(=O)C(CCCCB1OC(C)(C)C(C)(C)O1)(CN/C(=N/C(=O)OC(C)(C)C)NC(=O)OC(C)(C)C)NC(C)=O]

A mixture of ethyl 2-acetamido-2-(aminomethyl)-6-(4,4,5,5-tetramethyl-1,3,2-dioxaborolan-2-yl)hexanoate hydrochloride (300 mg, 0.75 mmol), N,N'-bis(tert-butoxycarbonyl)-1H-pyrazole-1-carboxamidine (280 mg, 0.90 mmol), triethylamine (114 µL, 0.82 mmol) and acetonitrile (3 mL) was stirred at room temperature for 50 hours. Then the solvent was evaporated under reduced pressure, the residue was dissolved in ethyl acetate (50 mL) and was washed with water (5 mL) and brine (10 mL), dried over MgSO$_4$, filtered and concentrated in vacuo to give a crude product. The crude material was purified by flash column chromatography, on silica gel (hexane/AcOEt 10:1 to 1:1) to give ethyl 2-acetamido-2-((2,3-bis(tert-butoxycarbonyl)guanidino)methyl)-6-(4,4,5,5-tetramethyl-1,3,2-dioxaborolan-2-yl)hexanoate (250 mg, 56%) as a white solid. ESI+MS: m/z=599.4/600.4 (M+H)$^+$, ESI-MS: m/z=597.5 (M−1)$^−$. $^1$H NMR (500 MHz, CDCl$_3$) δ 11.33 (s, 1H), 8.55-8.42 (m, 1H), 6.93 (s, 1H), 4.24-4.16 (m, 2H), 4.02 (dd, J=13.8, 7.5 Hz, 1H), 3.97 (dd, J=13.8, 5.1 Hz, 1H), 2.22-2.14 (m, 1H), 1.99 (s, 3H), 1.88-1.80 (m, 1H), 1.45 (s, 9H), 1.44 (s, 9H), 1.39-1.30 (m, 3H), 1.28 (t, J=7.1 Hz, 3H), 1.19 (s, 12H), 1.09-1.00 (m, 1H), 0.71 (t, J=7.8 Hz, 2H). Partial borane deprotection was observed during chromatography so 5-acetamido-5-((2,3-bis(tert-butoxycarbonyl)guanidino)methyl)-6-ethoxy-6-oxohexylboronic acid (120 mg) was obtain as a crude by-product.

Step B. 2-Amino-6-borono-2-(guanidinomethyl)hexanoic acid dihydrochloride

A mixture of ethyl 2-acetamido-2-((2,3-bis(tert-butoxycarbonyl)guanidino)methyl)-6-(4,4,5,5-tetramethyl-1,3,2-dioxaborolan-2-yl)hexanoate (220 mg, 0.367 mmol), methanol (1 mL) and 3 N HCl (4 mL) was heated under reflux for 4 h. Then 0.5 mL of concentrated hydrochloric acid was added and the heating was continued for 2 h. After cooling to room temperature the reaction mixture was concentrated in vacuo and the residue was purified by preparative HPLC (0.1-10% MeCN in water) to give 2-amino-6-borono-2-(guanidinomethyl)hexanoic acid dihydrochloride (20 mg, 17%) as a white solid. ESI+MS: m/z=229.1 (M−18+H)$^+$, 211.2 (M−36+H)$^+$, ESI-MS: m/z=227.3 (M−18−1)$^−$. $^1$H NMR (500 MHz, D$_2$O) δ 3.69 (d, J=15.6 Hz, 1H), 3.49 (d, J=15.6 Hz, 1H), 1.84-1.75 (m, 1H), 1.75-1.62 (m, 1H), 1.31-1.21 (m, 3H), 1.16-1.03 (m, 1H), 0.62 (t, J=7.5 Hz, 2H).

Example 3. 2-Amino-6-borono-2-(ureidomethyl)hexanoic acid hydrochloride

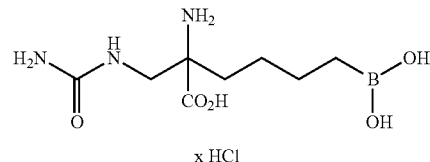 [SMILES: NC(=O)NCC(N)(CCCCB(O)O)C(=O)O]

A mixture of crude 5-acetamido-5-((2,3-bis(tert-butoxycarbonyl)guanidino)methyl)-6-ethoxy-6-oxohexylboronic acid (120 mg, 0.232 mmol) (obtained as a by-product in example 2 step A), methanol (1 mL) and 2 N HCl (0.5 mL) was heated under reflux for 3 h. Then methanol was evaporated and 1 mL of concentrated hydrochloric acid was added to the reaction mixture and the heating was continued for 6 h. After cooling to room temperature the reaction mixture was concentrated in vacuo and the residue was purified by preparative HPLC (0.1-10% MeCN in water) to give 2-amino-6-borono-2-(ureidomethyl)hexanoic acid hydrochloride (3.5 mg, 5%) as a colorless film. ESI+MS: m/z=248.1 (M+H)$^+$. $^1$H NMR (500 MHz, D$_2$O) δ 3.73 (d, J=14.9 Hz, 1H), 3.47 (d, J=14.9 Hz, 1H), 1.94-1.84 (m, 1H), 1.82-1.72 (m, 1H), 1.38-1.08 (m, 4H), 0.63 (t, J=7.5 Hz, 2H).

Example 4. 2-Amino-6-borono-2-(((N,N-dimethylsulfamoyl)amino)methyl)hexanoic acid hydrochloride

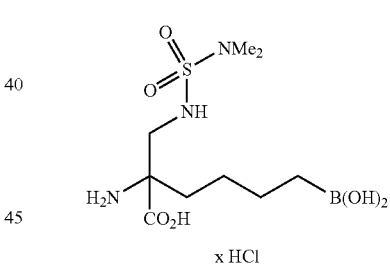

Step A. Ethyl 2-acetamido-2-(((N,N-dimethylsulfamoyl)amino)methyl)-6-(4,4,5,5-tetramethyl-1,3,2-dioxaborolan-2-yl)hexanoate

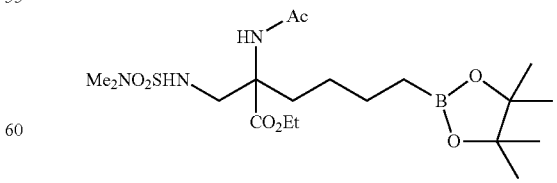

A solution of N,N-dimethylsulfamoyl chloride (60 µL; 0.56 mmol) in dichloromethane (2 mL) was added dropwise to a solution of ethyl 2-acetamido-2-(aminomethyl)-6-(4,4,5,5-tetramethyl-1,3,2-dioxaborolan-2-yl)hexanoate hydrochloride (200 mg, 0.51 mmol) and triethylamine in dichloromethane (3 mL) at 0° C. The reaction was allowed to warm to room temperature and then stirred for 20 h. The reaction mixture was diluted with dichloromethane (50 mL), washed with 1 M KHSO$_4$ (aq) (10 mL), water (10 mL) and 5% NaHCO$_3$(aq) (10 mL) and dried over MgSO$_4$, filtered and concentrated in vacuo to afford a crude product. The crude product was purified by flash column chromatography, on silica gel (hexane/AcOEt, 1:1) to give 60 mg (25%) of the desired product as a white solid. ESI+MS: m/z=464.1 (M+H)$^+$, ESI-MS: m/z=462.4 (M−1)$^−$. $^1$H NMR (700 MHz, CDCl$_3$) δ 6.46 (s, 1H), 4.69 (s, 1H), 4.32-4.19 (m, 2H), 3.88-3.92 (m, 1H), 3.50-3.55 (m, 1H), 2.79 (s, 6H), 2.29-2.21 (m, 1H), 2.05 (s, 3H), 1.74-1.68 (m, 1H), 1.40-1.46 (m, 2H), 1.33 (t, J=7.1 Hz, 3H), 1.25 (s, 12H), 0.93-0.87 (m, 2H), 0.76 (t, J=7.9 Hz, 2H).

Step B. 2-Amino-6-borono-2-(((N,N-dimethylsulfamoyl)amino)methyl)hexanoic acid hydro-chloride A mixture of ethyl 2-acetamido-2-(((N,N-dimethylsulfamoyl)amino)methyl)-6-(4,4,5,5-tetramethyl-1,3,2-dioxaborolan-2-yl)hexanoate (50 mg, 0.108 mmol), methanol (0.1 mL) and 2 N HCl (1 mL) was heated under reflux for 10 h. After cooling to room temperature the reaction mixture was concentrated in vacuo and the residue was purified by preparative HPLC (0.1-10% MeCN in water) to give 2 mg (5%) of the desired product as a colorless glass. ESI+MS: m/z=312.2 (M+H)$^+$, 294.2 (M−18+H)$^+$, ESI-MS: m/z=292.4 (M−18−1)$^−$. $^1$H NMR (500 MHz, D$_2$O) δ 3.49 (d, J=14.9 Hz, 1H), 3.29 (d, J=14.9 Hz, 1H), 2.70 (s, 6H), 1.78-1.69 (m, 1H), 1.68-1.59 (m, 1H), 1.37-1.21 (m, 3H), 1.21-1.04 (m, 1H), 0.75-0.58 (m, 2H).

Example 5. (5-Amino-5-(((N-benzylsulfamoyl)amino)methyl)-6-ethoxy-6-oxohexyl)boronic acid hydrochloride

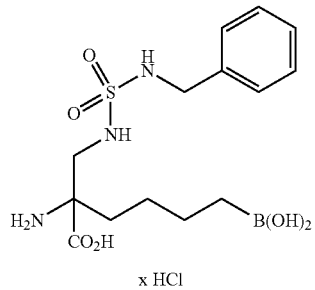 [SMILES: NC(CCCCB(O)O)(CNS(=O)(=O)NCc1ccccc1)C(=O)O]

x HCl

Step A. Ethyl 2-acetamido-2-(((N-benzyl-N-(tert-butoxycarbonyl)sulfamoyl)amino)methyl)-6-(4,4,5,5-tetramethyl-1,3,2-dioxaborolan-2-yl)hexanoate To a solution of ethyl 2-acetamido-2-(((N-(tert-butoxycarbonyl)sulfamoyl)amino)methyl)-6-(4,4,5,5-tetramethyl-1,3,2-dioxaborolan-2-yl)hexanoate (200 mg; 0.373 mmol), benzyl alcohol (70 μL; 0.679 mmol) and triphenylphosphine (178 mg; 0.679 mmol) in THF (1 mL) was added dropwise a solution of diisopropyl azodicarboxylate (134 μL; 0.679 mmol) in THF (1 mL) at 0° C. under Ar. The reaction mixture was stirred at 0° C.-10° C. for 1.5 h. Next silica gel was added, the mixture was concentrated and subjected to silica gel column chromatography eluting with hexane/AcOEt (3:1) to give 200 mg (86%) of the desired product as a white solid. ESI+MS: m/z=626.3 (M+H)$^+$, 648.3 (M+Na)$^+$, ESI-MS: m/z=624.5 (M−1)$^−$. $^1$H NMR (500 MHz, CDCl$_3$) δ 7.40-7.26 (m, 5H), 6.31 (bs, 1H), 5.56 (dd, J=8.9, 5.1 Hz, 1H), 4.87 (d, J=15.7 Hz, 1H), 4.76 (d, J=15.7 Hz, 1H), 4.28-4.17 (m, 2H), 3.58 (dd, J=12.4, 5.1 Hz, 1H), 3.12 (dd, J=12.3, 9.1 Hz, 1H), 2.16 (td, J=13.0, 4.5 Hz, 1H), 1.99 (s, 3H), 1.60-1.52 (m, 1H), 1.47 (s, 9H), 1.30-1.35 (m, 2H), 1.29 (t, J=7.1 Hz, 3H), 1.24-1.20 (m, 12H), 0.91-0.82 (m, 2H), 0.72 (t, J=7.8 Hz, 2H).

Step B. (5-Amino-5-(((N-benzylsulfamoyl)amino)methyl)-6-ethoxy-6-oxohexyl)boronic acid hydrochloride A mixture of ethyl 2-acetamido-2-(((N-benzyl-N-(tert-butoxycarbonyl)sulfamoyl)amino)-methyl)-6-(4,4,5,5-tetramethyl-1,3,2-dioxaborolan-2-yl)hexanoate (190 mg, 0.304 mmol), methanol (0.2 mL) and 2 N HCl (2 mL) was heated under reflux for 15 h. After cooling to room temperature the reaction mixture was concentrated in vacuo and the residue was purified by preparative HPLC (5-15% MeCN in water) to give 17 mg (13%) of the desired product as a colorless glass. ESI+MS: m/z=356.0 (M−18+H)$^+$, ESI-MS: m/z=372.1 (M−1)$^−$, 354.2 (M−18−1)$^−$. $^1$H NMR (500 MHz, D$_2$O) δ 7.35-7.17 (m, 5H), 4.05 (d, J=2.4 Hz, 2H), 3.12 (d, J=15.0 Hz, 1H), 2.95 (d, J=15.1 Hz, 1H), 1.70-1.50 (m, 2H), 1.31-1.12 (m, 3H), 1.03 (dt, J=12.2, 5.5 Hz, 1H), 0.61 (t, J=7.7 Hz, 2H).

Example 6. (5-Amino-6-ethoxy-5-(((N-methylsulfamoyl)amino)methyl)-6-oxohexyl)boronic acid hydrochloride

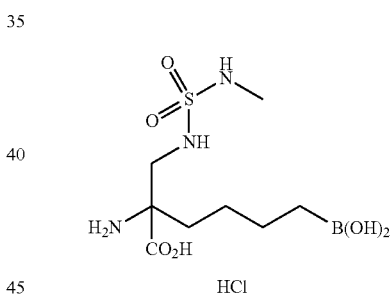

HCl

Step A. Ethyl 2-acetamido-2-(((N-(tert-butoxycarbonyl)-N-methylsulfamoyl)amino)methyl)-6-(4,4,5,5-tetramethyl-1,3,2-dioxaborolan-2-yl)hexanoate

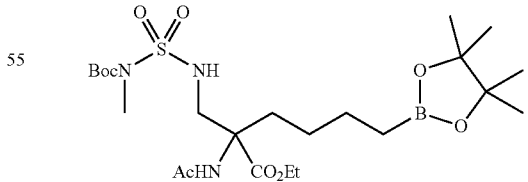

To a solution of ethyl 2-acetamido-2-(((N-(tert-butoxycarbonyl)sulfamoyl)amino)methyl)-6-(4,4,5,5-tetramethyl-1,3,2-dioxaborolan-2-yl)hexanoate (170 mg; 0.317 mmol), methanol (17 μL; 0.413 mmol) and triphenylphosphine (108 mg; 0.413 mmol) in THF (1 mL) was added dropwise a solution of diisopropyl azodicarboxylate (81 μL; 0.413 mmol) in THF (0.8 mL) at 0° C. under Ar. The reaction mixture was stirred at 0° C.-10° C. for 2 h followed by additional amount of methanol (10 µL) was added and stirring was continued for 0.5 h. Then the mixture was concentrated and subjected to silica gel column chromatography eluting with hexane/AcOEt (10:1 to 3:1) to give 65 mg (37%) of the desired product as a white solid. ESI+MS: m/z=572.2 (M+Na)$^+$, ESI-MS: m/z=548.4 (M−1)$^−$. $^1$H NMR (500 MHz, CDCl$_3$) δ 6.31 bs, 1H), 5.53 (dd, J=8.9, 5.1 Hz, 1H), 4.27-4.19 (m, 2H), 3.79 (dd, J=12.4, 5.3 Hz, 1H), 3.35 (dd, J=12.2, 8.9 Hz, 1H), 3.19 (s, 3H), 2.26 (ddd, J=12.9, 9.7, 4.4 Hz, 1H), 1.70-1.61 (m, 1H), 1.50 (s, 9H), 1.38-1.32 (m, 2H), 1.28 (t, J=7.1 Hz, 3H), 1.20 (s, 12H), 1.10-0.95 (m, 1H), 0.86-0.90 (m, 1H), 0.71 (t, J=7.8 Hz, 2H).

Step B. (5-Amino-6-ethoxy-5-(((N-methylsulfamoyl)amino)methyl)-6-oxohexyl)boronic acid hydrochloride A mixture of ethyl 2-acetamido-2-(((N-(tert-butoxycarbonyl)-N-methylsulfamoyl)amino)-methyl)-6-(4,4,5,5-tetramethyl-1,3,2-dioxaborolan-2-yl)hexanoate (60 mg, 0.109 mmol), methanol (0.1 mL) and 2 N HCl (1 mL) was heated under reflux for 4 h. After cooling to room temperature the reaction mixture was concentrated in vacuo and the residue was purified by preparative HPLC (0.1-10% MeCN in water) to give 10 mg (27%) of (5-amino-6-ethoxy-5-(((N-methylsulfamoyl)amino)methyl)-6-oxohexyl)boronic acid hydrochloride as a colorless glass. ESI+MS: m/z=298.2 (M+H)$^+$, 280.2 (M−18+H)$^+$, ESI-MS: m/z=278.3 (M−18−1)$^−$. $^1$H NMR (500 MHz, D$_2$O) δ 3.45 (d, J=15.1 Hz, 1H), 3.20 (d, J=15.1 Hz, 1H), 2.48 (s, 3H), 1.75-179 (m, 1H), 1.62-1.66 (m, 1H), 1.33-1.19 (m, 3H), 1.17-1.04 (m, 1H), 0.63 (t, J=7.6 Hz, 2H).

Example 7. 2-Amino-6-borono-2-((3-methylguanidino)methyl)hexanoic acid hydrochloride

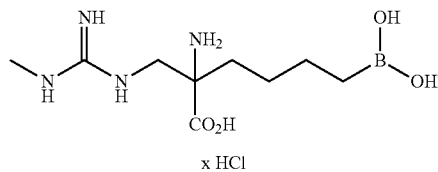 [SMILES: CNC(=N)NCC(N)(CCCCB(O)O)C(=O)O]

x HCl

Step A. Ethyl 2-(((benzyloxy)carbonyl)amino)-2-cyano-6-(4,4,5,5-tetramethyl-1,3,2-dioxaborolan-2-yl)hexanoate

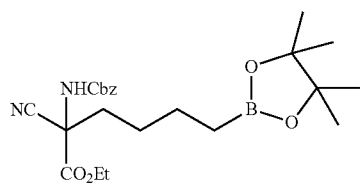 [SMILES: CCOC(=O)C(C#N)(CCCCB1OC(C)(C)C(C)(C)O1)NC(=O)OCc1ccccc1]

A sodium hydride (60% dispersion in mineral oil) (1.1 g, 27.4 mmol) was added to dry DMF (100 mL). After cooling in ice bath (0° C.) a solution of ethyl 2-(((benzyloxy)carbonyl)amino)-2-cyanoacetate (6.0 g, 22.9 mmol) in DMF (100 mL) was added dropwise. The reaction mixture was stirred for 30 min at 0° C. Then a solution of 2-(4-bromobutyl)-4,4,5,5-tetramethyl-1,3,2-dioxaborolane (7.22 g, 27.4 mmol) in dry DMF (50 mL) was added dropwise. The mixture was stirred overnight at room temperature. Next to the reaction mixture was added ethyl acetate (600 mL) and the mixture was washed with brine (300 mL), water (300 mL) and brine (300 mL). A organic layer was dried over MgSO$_4$ and concentrated. The product was purified by column chromatography on silica gel (hexane/AcOEt 5:1 to 3:1) to give a desired product (5.69 g, 56%) as a colorless oil. ESI+MS: m/z=467.0 (M+Na)$^+$, 445.0 (M+1)$^+$, 1H NMR (500 MHz, Chloroform-d) δ 7.43-7.29 (m, 5H), 5.71 (bs, 1H), 5.14 (s, 2H), 4.41-4.24 (m, 2H), 2.15 (d, J=7.4 Hz, 1H), 2.00 (t, J=11.2 Hz, 1H), 1.48 (dd, J=16.5, 7.4 Hz, 4H), 1.37-1.28 (m, 3H), 1.22 (d, J=5.2 Hz, 12H), 0.78 (q, J=5.4, 4.9 Hz, 2H).

Step B. Ethyl 2-(((benzyloxy)carbonyl)amino)-2-(((tert-butoxycarbonyl)amino)methyl)-6-(4,4,5,5-tetramethyl-1,3,2-dioxaborolan-2-yl)hexanoate

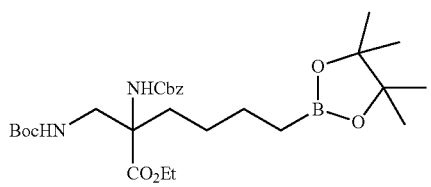 [SMILES: CCOC(=O)C(CCCCB1OC(C)(C)C(C)(C)O1)(CNC(=O)OC(C)(C)C)NC(=O)OCc1ccccc1]

Ethyl 2-(((benzyloxy)carbonyl)amino)-2-cyano-6-(4,4,5,5-tetramethyl-1,3,2-dioxaborolan-2-yl)hexanoate (5.59 g, 12.6 mmol) was dissolved in MeOH (215 mL). Then di-tert-butyl dicarbonate (5.5 g, 25.2 mmol) and nickel chloride hexahydrate (0.3 g, 1.3 mmol) was added to a reaction mixture at −8° C. To the resulting solution sodium borohydride (3.34 g, 88.2 mmol) was added portion-wise. The reaction mixture was stirred at room temperature overnight. Next additional portion of sodium borohydride (0.47 g, 12.6 mmol) and Boc$_2$O (1.37 g, 6.3 mmol) were added. After stirring at room temperature for 3 h a solvent was evaporated and a residue was divided between sat. NH$_4$Cl (100 mL) and AcOEt (200 mL). A organic layer was washed with sat. NH$_4$Cl (2×150 mL), brine (150 mL), dried over MgSO$_4$ and concentrated in vacuo. The crude product was purified by flash chromatography on silica gel (hexane/AcOEt, 3:1+ TEA (1%)) to give a desired product (2.47 g, 36%) as a colorless liquid. ESI+MS: m/z=571.1 (M+23)$^+$. 1H NMR (500 MHz, Chloroform-d) δ 7.33 (d, J=4.4 Hz, 4H), 7.29 (dt, J=9.1, 4.6 Hz, 1H), 5.85 (bs, 1H), 5.04 (s, 2H), 4.83 (bs, 1H), 4.26-4.12 (m, 2H), 3.72-3.69 (m, 4H), 2.12 (dd, J=13.8, 7.5 Hz, 1H), 1.83-1.80 (m, 4H), 1.72 (td, J=13.1, 3.8 Hz, 1H), 1.37 (s, 9H), 1.19 (d, J=4.9 Hz, 13H), 0.70 (t, J=7.8 Hz, 2H).

Step C. Ethyl 2-(aminomethyl)-2-(((benzyloxy)carbonyl)amino)-6-(4,4,5,5-tetramethyl-1,3,2-dioxaborolan-2-yl)hexanoate

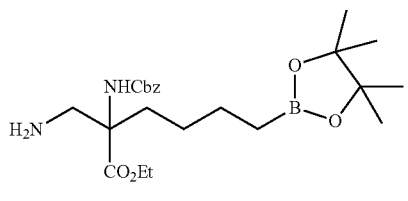

x HCl

A mixture of ethyl 2-(((benzyloxy)carbonyl)amino)-2-(((tert-butoxycarbonyl)amino)methyl)-6-(4,4,5,5-tetramethyl-1,3,2-dioxaborolan-2-yl)hexanoate (455 mg, 0.83 mmol) and HCl in ethyl acetate (2.6 M) (3.5 mL) was stirred at room temperature for 1.5 h. Then a solvent was evaporated to give ethyl 2-(aminomethyl)-2-(((benzyloxy)carbonyl)amino)-6-(4,4,5,5-tetramethyl-1,3,2-dioxaborolan-2-yl)hexanoate (410 mg, 100%) as a orange oil. ESI+MS: m/z=449.1 (M+1)$^+$. 1H NMR (700 MHz, Chloroform-d) δ 7.37 (d, J=6.4 Hz, 2H), 7.33 (t, J=7.4 Hz, 2H), 7.29 (d, J=7.1 Hz, 1H), 6.13 (s, 1H), 5.11 (q, J=12.2 Hz, 2H), 4.26 (s, 2H), 3.59 (d, J=66.0 Hz, 2H), 2.10 (s, 1H), 1.85-1.78 (m, 1H), 1.38 (dt, J=13.8, 7.0 Hz, 2H), 1.29-1.25 (m, 3H), 1.21 (s, 14H), 0.74 (t, J=7.8 Hz, 2H).

Step D. Ethyl 2-(((benzyloxy)carbonyl)amino)-2-((2,3-bis(tert-butoxycarbonyl)-3-methylguanidino)methyl)-6-(4,4,5,5-tetramethyl-1,3,2-dioxaborolan-2-yl)hexanoate

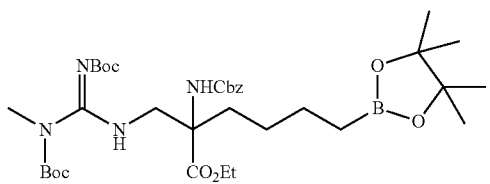

To a mixture of N,N'-bis(tert-butoxycarbonyl)-1H-pyrazole-1-carboxamidine (2 g, 6.44 mmol), triphenylphosphine (2.53 g, 9.67 mmol), MeOH (260 μL, 6.44 mmol) and dry THF (20 mL) was added dropwise DIAD (1.9 mL, 9.67 mmol) at 0° C. under argon. The reaction mixture was stirred at room temperature overnight. Then a solid was filtered off and the filtratrate was concentrated under reduced pressure. A residue was washed with hexane (6×50 mL). Hexane was evaporated and the residue was purified by column chromatography on silica gel (hexane/AcOEt, 7:1 to 5:1) to give tert-butyl (((tert-butoxycarbonyl)imino)(1H-pyrazol-1-yl)methyl)(methyl)carbamate (1.49 g, 71%) as a colorless oil. ESI+MS: m/z=347.1 (M+1)$^+$. 1H NMR (700 MHz, Chloroform-d) δ 8.02 (s, 1H), 7.71 (d, J=1.1 Hz, 1H), 6.45 (ddd, J=8.7, 2.7, 1.6 Hz, 1H), 3.27 (s, 3H), 1.54 (s, 9H), 1.32 (s, 9H).

A mixture of ethyl 2-(aminomethyl)-2-(((benzyloxy)carbonyl)amino)-6-(4,4,5,5-tetramethyl-1,3,2-dioxaborolan-2-yl)hexanoate (200 mg, 0.41 mmol), tert-butyl (((tert-butoxycarbonyl)-imino)(1H-pyrazol-1-yl)methyl)(methyl)carbamate (161 mg, 0.50 mmol) (obtained as above), MeCN (1.5 mL) and triethylamine (70 μL, 0.50 mmol) was stirred at RT for 3 days. Then a solvent was evaporated. A residue was dissolved in ethyl acetate (5 mL) and washed with water (3 mL) and brine (3 mL). A organic layer was dried over MgSO$_4$ and concentrated. The crude product was purified by flash column chromatography (hexane/AcOEt 5:1 to 3:1) to give ethyl 2-(((benzyloxy)carbonyl)amino)-2-((2,3-bis(tert-butoxycarbonyl)-3-methylguanidino)methyl)-6-(4,4,5,5-tetramethyl-1,3,2-dioxaborolan-2-yl)hexanoate (115 mg, 40%) as a colorless film. ESI+MS: m/z=706.2 (M+1)$^+$, ESI-MS: m/z=621.2 (M−1)$^−$. 1H NMR (700 MHz, Chloroform-d) δ 7.36 (d, J=4.5 Hz, 4H), 7.32 (dq, J=8.4, 4.2, 3.6 Hz, 1H), 5.86 (bs, 1H), 5.10 (s, 2H), 4.31-4.18 (m, 2H), 4.08-3.94 (m, 1H), 3.77-3.56 (m, 2H), 3.04 (s, 3H), 1.76-1.65 (m, 1H), 1.56 (td, J=12.2, 10.9, 7.3 Hz, 3H), 1.49 (d, J=10.3 Hz, 18H), 1.42-1.34 (m, 2H), 1.26 (s, 3H), 1.23 (s, 12H), 0.74 (t, J=7.9 Hz, 2H).

Step E. 2-Amino-6-borono-2-((3-methylguanidino)methyl)hexanoic acid hydrochloride A mixture of ethyl 2-(((benzyloxy)carbonyl)amino)-2-((2,3-bis(tert-butoxycarbonyl)-3-methylguanidino)methyl)-6-(4,4,5,5-tetramethyl-1,3,2-dioxaborolan-2-yl)hexanoate (60 mg, 0.085 mmol), 6 N HCl (1.5 mL) was heated under reflux for 3.5 h. Then the mixture was concentrated and the crude product was purified by preparative HPLC (0.1-2% MeCN in water) to give 2-amino-6-borono-2-((3-methylguanidino)methyl)hexanoic acid hydrochloride (8 mg, 32%) as a white solid. ESI+MS: m/z=243.1(M−18+1)$^+$, 225.0 (M−36+1)$^+$, ESI-MS: m/z=241.0 (M−18−1)$^−$. $^1$H NMR (700 MHz, Deuterium Oxide) δ 3.68 (d, J=15.4 Hz, 1H), 3.43 (d, J=15.5 Hz, 1H), 2.71 (s, 3H), 1.84-1.74 (m, 1H), 1.68-1.59 (m, 1H), 1.32-1.22 (m, 3H), 1.15-1.07 (m, 1H), 0.69-0.58 (m, 2H).

Example 8. 6-Borono-2-(methylamino)-2-((sulfamoylamino)methyl)hexanoic acid hydrochloride

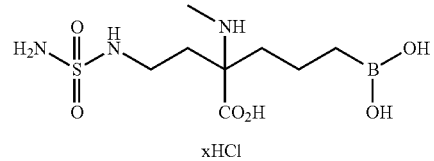 [SMILES: CNC(CCCB(O)O)(CCNS(N)(=O)=O)C(=O)O]

xHCl

Step A. tert-Butyl 2-((tert-butoxycarbonyl)(methyl)amino)-2-cyano-6-(4,4,5,5-tetramethyl-1,3,2-dioxaborolan-2-yl)hexanoate

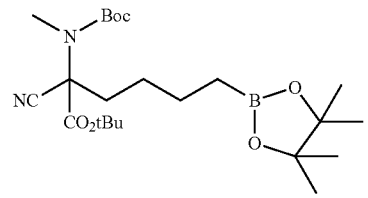

To a solution of tert-butyl 2-((tert-butoxycarbonyl)amino)-2-cyano-6-(4,4,5,5-tetramethyl-1,3,2-dioxaborolan-2-yl)hexanoate (133 mg, 0.30 mmol) (example 1, method B, step A) in DMF (1.5 mL) was added sodium hydride (60% dispersion in mineral oil) (14.5 mg, 0.36 mmol) at RT. Then to the reaction mixture was added methyl iodide (38 μl, 0.61 mmol) and stirred for 3 h at RT. Next the reaction was quenched with H$_2$O (20 mL) and washed with Et$_2$O (3×15 mL). The combined organic layers were washed with saturated NH$_4$Cl (15 mL), dried over MgSO$_4$ and concentrated under reduced pressure to give a desired product (115 mg, 85%) as a colorless oil. ESI+MS: m/z=393.1 (M−Pin+Na)$^+$, 397.2 (M−t-Bu+1)$^+$. 1H NMR (700 MHz, Chloroform-d) δ 3.02 (s, 3H), 2.13-2.00 (m, 2H), 1.69-1.58 (m, 1H), 1.52 (d, J=7.5 Hz, 21H), 1.26 (s, 11H), 1.23 (t, J=7.0 Hz, 1H), 0.84 (t, J=7.6 Hz, 2H).

Step B. tert-Butyl 2-(aminomethyl)-2-((tert-butoxycarbonyl)(methyl)amino)-6-(4,4,5,5-tetramethyl-1,3,2-dioxaborolan-2-yl)hexanoate

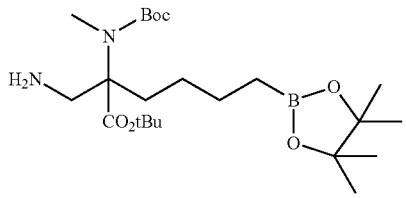 [SMILES: CN(C(=O)OC(C)(C)C)C(CN)(CCCCB1OC(C)(C)C(C)(C)O1)C(=O)OC(C)(C)C]

Sodium borohydride (66 mg, 1.75 mmol) was added portion-wise (by 30 min) to a mixture of tert-butyl 2-((tert-butoxycarbonyl)(methyl)amino)-2-cyano-6-(4,4,5,5-tetramethyl-1,3,2-dioxaborolan-2-yl)hexanoate (113 mg, 0.25 mmol), cobalt(II) chloride hexahydrate (65 mg, 0.50 mmol) and MeOH (2 mL) at −20° C. under argon. After stirring for 3 h the mixture was quenched with saturated NH$_4$Cl (20 mL) and washed with AcOEt (3×15 mL). The combined organic layers were dried over MgSO$_4$ and concentrated in vacuo to give the crude product (138 mg, 100%) as a white solid. ESI+MS: m/z=457.2 (M+1)$^+$. The crude product was used to the next step without any further purification.

Step C. tert-Butyl 2-((tert-butoxycarbonyl)(methyl)amino)-2-(((N-(tert-butoxycarbonyl)-sulfamoyl)amino)methyl)-6-(4,4,5,5-tetramethyl-1,3,2-dioxaborolan-2-yl)hexanoate

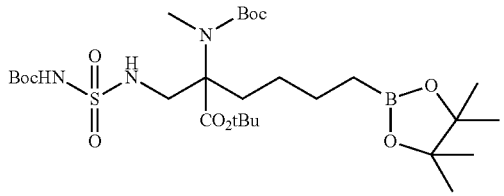 [SMILES: CN(C(=O)OC(C)(C)C)C(CCCCB1OC(C)(C)C(C)(C)O1)(CNS(=O)(=O)NC(=O)OC(C)(C)C)C(=O)OC(C)(C)C]

A mixture of (tert-butoxycarbonyl)((4-(methylimino)pyridin-1(4H)-yl)sulfonyl)amide (commercially available) (48 mg, 0.16 mmol), tert-butyl 2-(aminomethyl)-2-((tert-butoxycarbonyl)(methyl)amino)-6-(4,4,5,5-tetramethyl-1,3,2-dioxaborolan-2-yl)hexanoate (60 mg, 0.13 mmol), dichloromethane (0.5 mL) and triethylamine (18 μL, 0.13 mmol) was stirred at room temperature for 24 h. Next the mixture was diluted with DCM (5 mL) and filtered. The filtrate was washed with water (2×2 mL), dried over MgSO$_4$ and concentrated. The crude product was purified by flash column chromatography on silica gel using hexane/AcOEt (10:1) as an eluent to afford 9 mg (11%) a desired product as a white solid. ESI+MS: m/z=658.3 (M+Na)$^+$, ESI-MS: m/z=634.3 (M−1)$^-$. 1H NMR (700 MHz, Chloroform-d) δ 3.74 (dd, J=13.6, 5.3 Hz, 1H), 3.50 (dd, J=13.5, 8.7 Hz, 1H), 2.94 (s, 3H), 1.93 (td, J=12.7, 3.9 Hz, 1H), 1.72 (td, J=12.7, 3.8 Hz, 1H), 1.51 (s, 9H), 1.46 (s, 9H), 1.48 (s, 9H), 1.39-1.45 (m, 2H), 1.27 (s, 12H), 1.24-1.18 (m, 1H), 0.91 (td, J=7.1, 2.3 Hz, 1H), 0.82 (dt, J=11.4, 8.3 Hz, 2H).

Step D. 6-Borono-2-(methylamino)-2-((sulfamoylamino)methyl)hexanoic acid hydrochloride To tert-butyl 2-((tert-butoxycarbonyl)(methyl)amino)-2-(((N-(tert-butoxycarbonyl)sulfamoyl)-amino)methyl)-6-(4,4,5,5-tetramethyl-1,3,2-dioxaborolan-2-yl)hexanoate (9 mg, 0.014 mmol) was added 4 M HCl in dioxane (1 mL) and stirred at room temperature for 2 h. Then to the reaction mixture was added 2 N HCl (aq) (1 mL) and stirred at RT overnight. The crude product was purified by preparative HPLC (0.1-5% MeCN in water) to give 6-borono-2-(methylamino)-2-((sulfamoylamino)methyl)hexanoic acid hydrochloride (3.1 mg, 66%) as a white solid. ESI+MS: m/z=280.2 (M−18+1)$^+$, ESI-MS: m/z=296.1 (M−1), 278.1 (M−18−1). 1H NMR (700 MHz, Deuterium Oxide) δ 3.52 (d, J=15.1 Hz, 1H), 3.41 (d, J=15.1 Hz, 1H), 2.62 (s, 3H), 1.82-1.68 (m, 2H), 1.36 (p, J=7.4 Hz, 2H), 1.23 (qq, J=12.4, 7.2, 6.1 Hz, 1H), 1.19-1.09 (m, 1H), 0.76-0.67 (m, 2H).

Example 9. 6-Borono-2-(guanidinomethyl)-2-(methylamino)hexanoic acid dihydrochloride

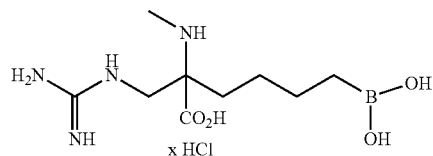 [SMILES: CNC(CCCCB(O)O)(CNC(=N)N)C(=O)O]

Step A. tert-Butyl 2-((2,3-bis(tert-butoxycarbonyl)guanidino)methyl)-2-((tert-butoxycarbonyl)-(methyl)amino)-6-(4,4,5,5-tetramethyl-1,3,2-dioxaborolan-2-yl)hexanoate

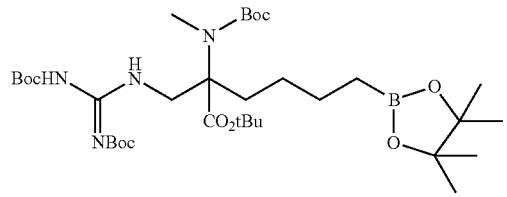

A mixture of tert-butyl 2-(aminomethyl)-2-((tert-butoxycarbonyl)(methyl)amino)-6-(4,4,5,5-tetramethyl-1,3,2-dioxaborolan-2-yl)hexanoate (67 mg, 0.15 mmol) (example 8, step B), N,N'-bis(tert-butoxycarbonyl)-1H-pyrazole-1-carboxamidine (56 mg, 0.18 mmol), triethylamine (21 μL, 0.15 mmol) and MeCN (1.5 mL) was stirred at room temperature for 4 h. Then a solvent was evaporated and a residue was dissolved in ethyl acetate (4 mL) and was washed with water (2 mL) and brine (2 mL). The organic layer was dried over MgSO$_4$ and concentrated under reduced pressure. The crude product was purified by flash column chromatography on silica gel (hexane/AcOEt 15:1 to 10:1) to give 50 mg (48%) of a desired product as a white solid. ESI+MS: m/z=699.8 (M+1)$^+$, 1H NMR (700 MHz, Chloroform-d) δ 4.11-4.01 (m, 1H), 3.79-3.67 (m, 1H), 2.87 (s, 3H), 1.86-1.76 (m, 1H), 1.74-1.65 (m, 1H), 1.59 (s, 9H), 1.55 (s, 9H), 1.48 (s, 9H), 1.44 (s, 9H), 1.28-1.27 (m, 1H), 1.24 (s, 12H), 0.90 (t, J=7.1 Hz, 3H), 0.80-0.78 (m, 2H).

Step B. 6-Borono-2-(guanidinomethyl)-2-(methylamino)hexanoic acid dihydrochloride To tert-butyl 2-((2,3-bis(tert-butoxycarbonyl)guanidino)methyl)-2-((tert-butoxycarbonyl)-(methyl)amino)-6-(4,4,5,5-tetramethyl-1,3,2-dioxaborolan-2-yl)hexanoate (50 mg, 0.07 mmol) was added 4 N HCl in dioxane (2.3 mL) and stirred at room temperature for 1 h. Then to the reaction mixture was added 2 N HCl (aq) (1 mL) and stirring was continued overnight. Next the mixture was concentrated and to the residue was added additional portion of 2 N HCl (aq)

(0.5 mL) and heated under reflux for 30 min. The solvent was evaporated and the crude product was purified by preparative HPLC (0.1-2% MeCN in water) to give 6-borono-2-(guanidinomethyl)-2-(methylamino)hexanoic acid dihydrochloride (15 mg, 72%) as a colorless film. ESI+MS: m/z=243.1(M−18+1)$^+$, 225.0 (M−36+1)$^+$, ESI-MS: m/z=259.1 (M−1)$^−$, 241.1(M−18−1)$^−$. 1H NMR (700 MHz, Deuterium Oxide) δ 3.67 (d, J=15.7 Hz, 1H), 3.51 (d, J=15.7 Hz, 1H), 2.54 (s, 3H), 1.80-1.71 (m, 1H), 1.71-1.62 (m, 1H), 1.34-1.25 (m, 2H), 1.25-1.15 (m, 1H), 1.12-1.05 (m, 1H), 0.65 (t, J=7.9 Hz, 2H).

Example 10.
2-Amino-6-borono-2-(2-sulfamoylethyl)hexanoic acid hydrochloride

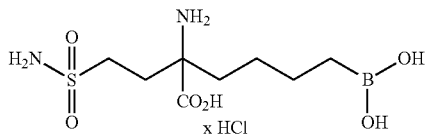 [SMILES: NC(CCCCB(O)O)(CCS(N)(=O)=O)C(=O)O]

Step A.
N,N-Bis(4-methoxybenzyl)ethenesulfonamide

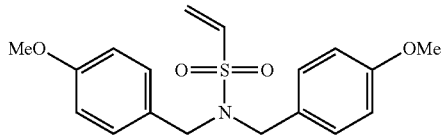 [SMILES: C=CS(=O)(=O)N(Cc1ccc(OC)cc1)Cc1ccc(OC)cc1]

To a solution of 2-chloroethanesulfonyl chloride (2 mL, 19 mmol) in dichloromethane (95 mL) was added dropwise triethylamine (2.64 mL, 19 mmol) at −72° C. under argon. The resulting mixture was stirred at this temperature for 10 min. Then the reaction mixture was warmed to room temperature and stirred for 2 h. After this time bis-(4-methoxybenzyl)-amine (4.94 g, 19 mmol) and TEA (3.17 mL, 23 mmol) were added at 0° C. After stirring at room temperature for 2 h the solvent was evaporated to give 6.87 g of the crude product (100%). 1H NMR (700 MHz, Chloroform-d) δ 7.27-7.19 (m, 4H), 6.93-6.88 (m, 4H), 6.32 (dd, J=16.5, 9.8 Hz, 1H), 6.22 (d, J=16.5 Hz, 1H), 5.87 (d, J=9.8 Hz, 1H), 4.22 (s, 4H), 3.84 (s, 6H). The crude product was used to the next step without any further purification.

Step B. tert-Butyl 4-(N,N-bis(4-methoxybenzyl) sulfamoyl)-2-((diphenylmethylene)amino)-butanoate

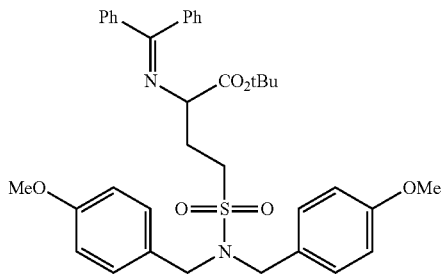 [SMILES: COc1ccc(CN(Cc2ccc(OC)cc2)S(=O)(=O)CCC(N=C(c2ccccc2)c2ccccc2)C(=O)OC(C)(C)C)cc1]

A mixture of N,N-bis(4-methoxybenzyl)ethenesulfonamide (2 g, 5.76 mmol), N-(diphenyl-methylene)glycine tert-butyl ester (1.70 g, 5.76 mmol), TBABr (186 mg, 0.58 mmol), cesium carbonate (5.63 g, 17.27 mmol) and acetonitrile (100 mL) was stirred at room temperature overnight. Then additional amounts of N-(diphenylmethylene)glycine tert-butyl ester (0.85 g, 2.88 mmol), TBABr (186 mg, 0.58 mmol) and cesium carbonate (3.75 g, 11.51 mmol) were added. After stirring at room temperature for 3 h the reaction mixture was warmed to 50° C. and stirring was continued for 20 h. The solvent was evaporated and the residue was purified by flash column chromatography on silica gel (AcOEt/hexane 1:5) to afford tert-butyl 4-(N,N-bis(4-methoxybenzyl)sulfamoyl)-2-((diphenylmethylene)amino) butanoate (580 mg, 15%) as a yellow oil. ESI+MS: m/z=480.0 (M−diphenylmethylene+1)$^+$, 502.1 (M−diphenylmethylene+Na)$^+$. 1H NMR (500 MHz, Chloroform-d) δ 7.64 (d, J=7.3 Hz, 2H), 7.51-7.47 (m, 1H), 7.45-7.38 (m, 5H), 7.34 (t, J=7.6 Hz, 2H), 7.19 (d, J=8.6 Hz, 4H), 6.80 (d, J=8.6 Hz, 4H), 4.24 (s, 4H), 4.00 (dd, J=7.2, 4.6 Hz, 1H), 3.76 (s, 6H), 3.14-2.96 (m, 2H), 2.49-2.35 (m, 1H), 2.31-2.24 (m, 1H), 1.43 (s, 9H).

Step C. tert-Butyl (E)-2-(2-(N,N-bis(4-methoxybenzyl)sulfamoyl)ethyl)-2-((diphenylmethylene)-amino) hex-4-enoate

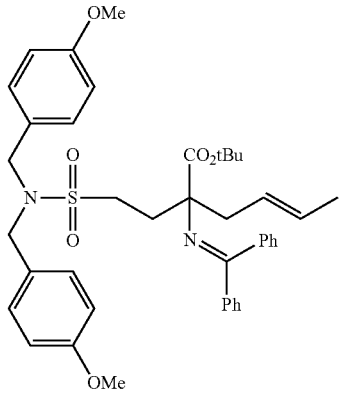 [SMILES: C/C=C/CC(CCS(=O)(=O)N(Cc1ccc(OC)cc1)Cc1ccc(OC)cc1)(N=C(c1ccccc1)c1ccccc1)C(=O)OC(C)(C)C]

To a solution of tert-butyl 4-(N,N-bis(4-methoxybenzyl) sulfamoyl)-2-((diphenylmethylene)-amino)butanoate (426 mg, 0.66 mmol) in THF (5 mL) was added dropwise KHMDS (0.5 M in toluene) (1.46 mL, 0.73 mmol) at −70° C. under argon. After stirring at −70° C. for 45 min, crotyl bromide (75 μL, 0.73 mmol) was added and stirred for 1.5 h at −70° C. After this time the mixture was warmed to room temperature and stirred overnight. Next, additional amount of crotyl bromide (14 μL) was added and the mixture was stirred for 1 h. Then the volatile materials were removed under reduced pressure and the residue was dissolved in AcOEt (100 mL), washed with sat. NH$_4$Cl (2×30 mL) and brine (30 mL). The organic layer was dried over MgSO$_4$ and concentrated. A crude product was purified by flash column chromatography on silica gel (AcOEt/hexane 1:7) to give a desired product (123 mg, 27%) as yellow oil. ESI+MS: m/z=721.1 (M+Na)$^+$, 698.2 (M+1)$^+$. 1H NMR (500 MHz, Chloroform-d) δ 7.51 (t, J=8.6 Hz, 2H), 7.39-7.34 (m, 4H), 7.29 (t, J=7.6 Hz, 2H), 7.19 (d, J=8.6 Hz, 6H), 6.80 (d, J=8.5 Hz, 4H), 5.45 (dd, J=15.1, 6.4 Hz, 1H), 5.40-5.28 (m, 1H), 4.29-4.18 (m, 4H), 3.77 (s, 6H), 3.42-3.29 (m, 1H), 3.23-3.10 (m, 1H), 2.46-2.39 (m, 2H), 2.32-2.20 (m, 2H), 1.63 (d, J=6.3 Hz, 3H), 1.28 (s, 9H).

Step D. tert-Butyl 2-(2-(N,N-bis(4-methoxybenzyl)sulfamoyl)ethyl)-2-((diphenylmethylene)-amino)-6-(4,4,5,5-tetramethyl-1,3,2-dioxaborolan-2-yl)hexanoate

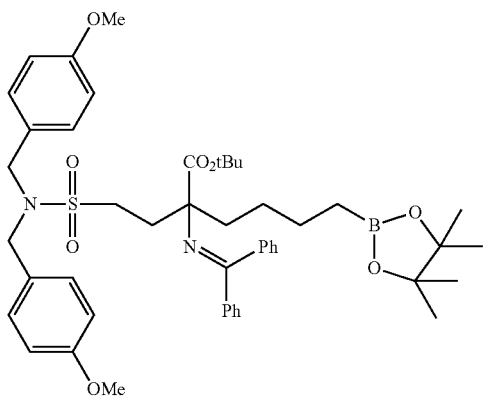 [SMILES: COc1ccc(CN(Cc2ccc(OC)cc2)S(=O)(=O)CCC(CCCCB2OC(C)(C)C(C)(C)O2)(N=C(c2ccccc2)c2ccccc2)C(=O)OC(C)(C)C)cc1]

A solution of tert-butyl (E)-2-(2-(N,N-bis(4-methoxybenzyl)sulfamoyl)ethyl)-2-((diphenyl-methylene)amino)hex-4-enoate (120 mg, 0.17 mmol) and 4,4,5,5-tetramethyl-1,3,2-dioxaborolane (33 µl, 0.22 mmol) in dichloromethane (3 mL) (flushed with argon) was added dropwise to a mixture of bis(1,5-cyclooctadiene)diiridium(I) dichloride (23 mg, 0.034 mmol), DPPE (27 mg, 0,068 mmol) in dichloromethane (3 mL) (flushed with argon). The resulting mixture was stirred at room temperature overnight and then subjected to flash column chromatography on silica gel (AcOEt/hexane 1:7 to 1:5) to give tert-butyl 2-(2-(N,N-bis(4-methoxybenzyl)sulfamoyl)ethyl)-2-((diphenylmethylene)amino)-6-(4,4,5,5-tetramethyl-1,3,2-dioxaborolan-2-yl)hexanoate (61 mg, 43%) as a colorless oil. ESI+MS: m/z=826.3 (M+1)⁺. 1H NMR (500 MHz, Chloroform-d) δ 7.56-7.47 (m, 2H), 7.39-7.31 (m, 4H), 7.28 (d, J=7.7 Hz, 2H), 7.24-7.16 (m, 6H), 6.80 (d, J=8.7 Hz, 4H), 4.24 (d, J=2.5 Hz, 4H), 3.77 (s, 6H), 3.33 (td, J=13.3, 4.0 Hz, 1H), 3.06 (td, J=13.3, 4.0 Hz, 1H), 2.48 (td, J=13.1, 4.0 Hz, 1H), 2.24-2.18 (m, 1H), 1.62 (d, J=13.5 Hz, 1H), 1.41 (d, J=12.6 Hz, 2H), 1.30 (s, 9H), 1.18 (d, J=5.6 Hz, 12H), 0.92-0.80 (m, 3H), 0.78-0.70 (m, 2H).

Step E. 2-Amino-6-borono-2-(2-sulfamoylethyl)hexanoic acid hydrochloride

To a mixture of tert-butyl 2-(2-(N,N-bis(4-methoxybenzyl)sulfamoyl)ethyl)-2-((diphenyl-methylene)amino)-6-(4,4,5,5-tetramethyl-1,3,2-dioxaborolan-2-yl)hexanoate (58 mg, 0.07 mmol), anisole (7 µL) and DCM (340 µL) was added dropwise TFA (340 µL, 4.4 mmol) and the mixture was stirred for 3 h at room temperature. Then the solvent was evaporated and additional portion of TFA (340 µL, 4.4 mmol) was added. The reaction mixture was stirred at RT overnight and concentrated followed by 2 N HCl (aq) (1.5 mL) was added and the mixture was stirred for 1 h. Then a mixture was washed with diethyl ether (2×3 mL). The aqueous layer was separated and concentrated. The crude product was purified by preparative HPLC (0.1-15% MeCN in water) to give 2-amino-6-borono-2-(2-sulfamoylethyl)hexanoic acid hydrochloride (17 mg, 76%) as a white solid. ESI+MS: m/z=265.2 (M−18+1)⁺, ESI-MS: m/z=263.3 (M−18−1)⁻. 1H NMR (500 MHz, Deuterium Oxide) δ 3.33-3.16 (m, 1H), 3.13-2.97 (m, 1H), 2.28-2.07 (m, 2H), 1.81-1.52 (m, 2H), 1.39-1.15 (m, 3H), 1.17-0.99 (m, 1H), 0.69-0.54 (m, 2H).

Example 11. (5-Amino-7-((N,N-dimethylsulfamoyl)amino)-5-(ethoxycarbonyl)heptyl)-boronic acid hydrochloride

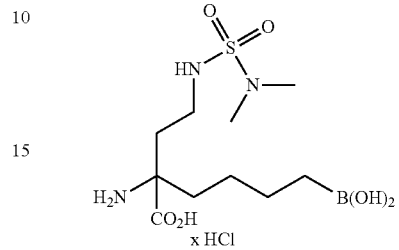

Step A. tert-Butyl (E)-2-((diphenylmethylene)amino)hex-4-enoate.

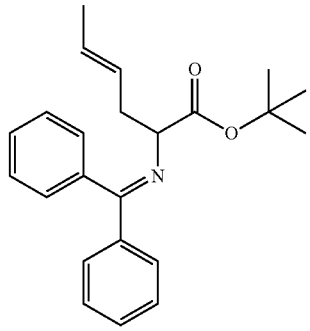 [SMILES: C/C=C/CC(N=C(c1ccccc1)c1ccccc1)C(=O)OC(C)(C)C]

A mixture of tert-butyl 2-((diphenylmethylene)amino)acetate (5 g; 0.017 mol), crotyl bromide (2.46 mL; 0.02 mol), cesium carbonate (12.18 g; 0.0374 mol), tetrabutylammonium bromide (0.55 g; 0.0017 mol) and acetonitrile (100 mL) was stirred for 5 hours. Next, the solvent was removed under reduced pressure and the residue was dissolved in ethyl acetate (150 mL) and the mixture was washed with water (2×30 mL) and brine (50 mL), dried over MgSO₄, filtered and concentrated in vacuo to afford 6.5 g (100%) of a desired product as a yellow liquid. The crude product was used to the next step without any further purification. ESI+MS: m/z=350.2 (M+H)⁺.

Step B. tert-Butyl (E)-2-(cyanomethyl)-2-((diphenylmethylene)amino)hex-4-enoate

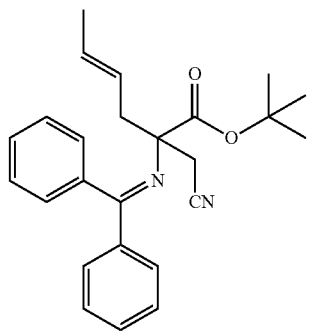 [SMILES: C/C=C/CC(CC#N)(N=C(c1ccccc1)c1ccccc1)C(=O)OC(C)(C)C]

A solution of KHMDS in toluene (0.5 M; 11 mL; 5.5 mmol) was added dropwise to a solution of tert-butyl (E)-2-((diphenylmethylene)amino)hex-4-enoate (1.75 g; 5 mmol) in THF (15 mL) at −75° C., under Ar. The mixture was stirred at −75° C. for 45 min followed by bromoacetonitrile (0.38 mL; 5.5 mmol) was added dropwise. The mixture was stirred at −75° C. for 20 min and 75 min at room temperature. Next, the reaction mixture was quenched wit saturated aqueous solution of NH$_4$Cl (20 mL) and washed with AcOEt (2×25 mL). The combined organic layers were washed with saturated aqueous solution of NH$_4$Cl (2×20 mL) and brine (30 mL), dried over MgSO$_4$, filtered and concentrated in vacuo to afford a crude product as brown liquid. The crude product was purified by flash column chromatography, on silica gel (hexane/AcOEt, 30:1 to 5:1) to give 1.52 g (77%) of the desired product as a colorless liquid. ESI+MS: m/z=389.1 (M+H)$^+$, $^1$H NMR (700 MHz, CDCl$_3$) δ 7.61-7.56 (m, 1H), 7.46-7.37 (m, 5H), 7.34-7.29 (m, 2H), 7.26-7.20 (m, 2H), 5.75-5.65 (m, 1H), 5.54-5.43 (m, 1H), 2.80-2.77 (m, 1H), 2.76-2.72 (d, J=16.5 Hz, 1H), 2.71-2.66 (m, 1H), 2.64 (d, J=16.5 Hz, 1H), 1.71 (dd, J=6.5, 1.5 Hz, 3H), 1.38 (s, 9H).

Step C. tert-Butyl (E)-2-amino-2-(cyanomethyl)hex-4-enoate

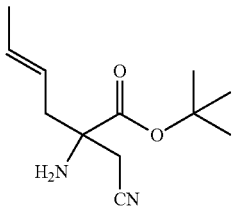

A mixture of tert-butyl (E)-2-(cyanomethyl)-2-((diphenylmethylene)amino)hex-4-enoate (1.5 g; 3.86 mmol), 1 M HCl (aq) (2.5 mL) and THF (5 mL) was stirred for 2 hours. Then the reaction mixture was washed with AcOEt (20 mL) and the organic layer was re-extracted to water (3×10 mL). The combined aqueous layers were washed with diethyl ether (2×5 mL) and alkalized with solid NaOH to pH=10 and washed with dichloromethane (3×15 mL). The combined organic layers were dried over MgSO$_4$, filtered and concentrated in vacuo to afford 0.5 g (53%) of a desired product as a colorless liquid. The crude product was used to the next step without any further purification. ESI+MS: m/z=225.3 (M+H)$^+$.

Step D. tert-Butyl (E)-2-((tert-butoxycarbonyl)amino)-2-(cyanomethyl)hex-4-enoate

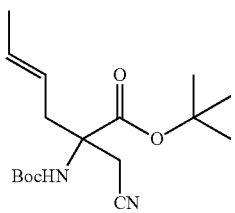 [SMILES: C/C=C/CC(CC#N)(NC(=O)OC(C)(C)C)C(=O)OC(C)(C)C]

To a solution of tert-butyl (E)-2-amino-2-(cyanomethyl)hex-4-enoate (0.48 g; 2.14 mmol) in THF/Water (1:1; 10 mL) were added di-tert-butyl dicarbonate (0.7 g; 3.21 mmol) and NaHCO$_3$ (0.45 g; 5.35 mmol). The mixture was stirred overnight. Then an additional amounts of Boc$_2$O (0.7 g) and NaHCO$_3$ (0.45 g) were added and stirred was continued overnight. The layers were separated. The aqueous layer was washed with ethyl acetate (2×30 mL). Next, the combined organic layers were washed with brine (30 mL), dried over MgSO$_4$, filtered and concentrated in vacuo. The crude product was purified by flash column chromatography, on silica gel (hexane/AcOEt, 50:1 to 10:1) to give 0.4 g (58%) of the desired product as a colorless liquid. ESI+MS: m/z=347.2 (M+Na)$^+$. $^1$H NMR (700 MHz, CDCl$_3$) δ 5.66 (dd, J=15.0, 6.6 Hz, 1H), 5.31 (s, 1H), 5.26 (dtd, J=9.1, 7.5, 1.7 Hz, 1H), 3.26-3.12 (m, 2H), 2.74 (dd, J=13.1, 7.0 Hz, 1H), 2.45 (dd, J=13.7, 7.6 Hz, 1H), 1.71 (dd, J=6.5, 1.4 Hz, 3H), 1.51 (s, 9H), 1.47 (s, 9H).

Step E. tert-Butyl 2-((tert-butoxycarbonyl)amino)-2-(cyanomethyl)-6-(4,4,5,5-tetramethyl-1,3,2-dioxaborolan-2-yl)hexanoate

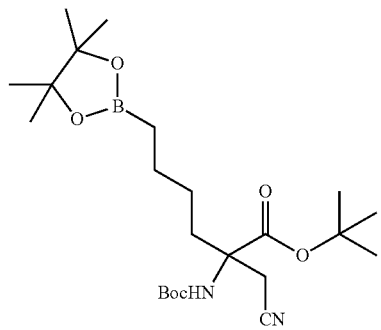 [SMILES: CC(C)(C)OC(=O)NC(CC#N)(CCCCB1OC(C)(C)C(C)(C)O1)C(=O)OC(C)(C)C]

A round-bottom flask charged with [Ir(cod)Cl]$_2$ (81 mg; 0.12 mmol) and 1,2-bis(diphenyl-phosphanyl)ethane (96 mg; 0.24 mmol) was flushed with argon. Dichloromethane (4 mL), 4,4,5,5-tetramethyl-1,3,2-dioxaborolane (0.26 mL; 1.8 mmol), and tert-butyl (E)-2-((tert-butoxy-carbonyl)amino)-2-(cyanomethyl)hex-4-enoate (0.39 g; 1.2 mmol) were added successively at room temperature. The mixture was then stirred at room temperature overnight. The solvent was evaporated and the residue was purified by flash column chromatography, on silica gel (hexane/AcOEt, 20:1 to 10:1) to give 0.37 g (68%) of the desired product as a white solid. ESI+MS: m/z=475.2 (M+Na)$^+$. $^1$H NMR (500 MHz, CDCl$_3$) δ 5.36 (s, 1H), 3.25 (d, J=16.9 Hz, 1H), 3.10 (d, J=16.9 Hz, 1H), 2.04 (td, J=12.6, 4.4 Hz, 1H), 1.78-1.66 (m, 1H), 1.48 (s, 9H), 1.46-1.37 (m+s, 11H), 1.27-1.17 (m+s, 14H), 0.81-0.70 (m, 2H).

Step F. tert-Butyl 2-(2-aminoethyl)-2-((tert-butoxycarbonyl)amino)-6-(4,4,5,5-tetramethyl-1,3,2-dioxaborolan-2-yl)hexanoate

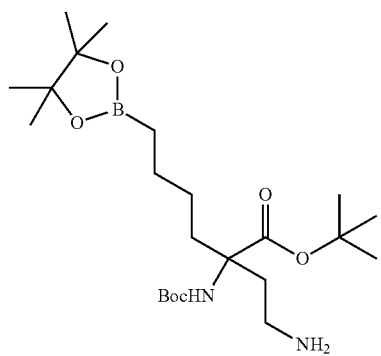 [SMILES: CC(C)(C)OC(=O)NC(CCN)(CCCCB1OC(C)(C)C(C)(C)O1)C(=O)OC(C)(C)C]

To a solution of tert-butyl 2-((tert-butoxycarbonyl)amino)-2-(cyanomethyl)-6-(4,4,5,5-tetramethyl-1,3,2-dioxaborolan-2-yl)hexanoate (0.35 g; 0.774 mmol) and NiCl$_2$×6H$_2$O (37 mg; 0.16 mmol) in methanol (8 mL) sodium borohydride (205 mg; 5.42 mol) was added portionwise at 0° C. The mixture was stirred at room temperature for 0.5 h. Then the reaction mixture was quenched wit saturated aqueous solution of NH$_4$Cl (20 mL) and filtered through Celite. The filtrate was then washed with ethyl acetate (4×20 mL). The combined organic layers were washed with brine (20 mL), dried over MgSO$_4$, filtered and concentrated in vacuo to afford 0.35 g of a crude product. The crude product was used to the next step without any further purification. ESI+MS: m/z=457.2 (M+H)$^+$.

Step G. tert-Butyl 2-((tert-butoxycarbonyl)amino)-2-(2-((N,N-dimethylsulfamoyl)amino)ethyl)-6-(4,4,5,5-tetramethyl-1,3,2-dioxaborolan-2-yl)hexanoate

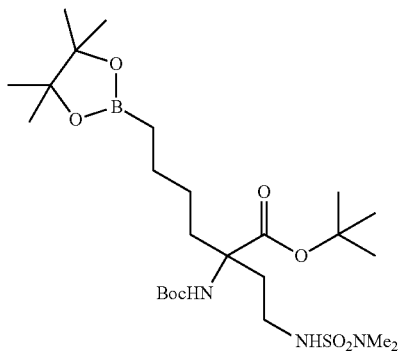

N,N-dimethylsulfamoyl chloride (32 μL; 0.3 mmol) was added dropwise to a solution of tert-butyl 2-(2-aminoethyl)-2-((tert-butoxycarbonyl)amino)-6-(4,4,5,5-tetramethyl-1,3,2-dioxa-borolan-2-yl)hexanoate (90 mg, 0.2 mmol) and triethylamine (96 uL; 0.69 mmol) in dichloromethane (1 mL) at 0° C. The reaction was allowed to warm to room temperature and then stirred for 20 h. The reaction mixture was diluted with dichloromethane (30 mL), washed with 1 M KHSO$_4$ (aq) (5 mL), dried over MgSO$_4$, filtered and concentrated in vacuo to afford a crude product. The crude product was purified by flash column chromatography, on silica gel (hexane/AcOEt, 20:1 to 1:1) to give 24 mg (22%) of the desired product as a white solid. ESI+MS: m/z=586.2 (M+Na)$^+$.

Step H. (5-Amino-7-((N,N-dimethylsulfamoyl)amino)-5-(ethoxycarbonyl)heptyl)boronic acid hydrochloride tert-Butyl 2-((tert-butoxycarbonyl)amino)-2-(2-((N,N-dimethylsulfamoyl)amino)ethyl)-6-(4,4,5,5-tetramethyl-1,3,2-dioxaborolan-2-yl)hexanoate (24 mg; 0.043 mmol) was treated with 4 M HCl in dioxane (1 mL). The mixture was stirred for 1 hour subsequent 2 M HCl (aq) (1 mL) was added and stirring was continued for 2 hours. The reaction mixture was concentrated under reduced pressure ant the residue was purified by preparative HPLC (0.1-15% MeCN in water) to give a desired product (1.2 mg, 7%) as a colorless glass. ESI+MS: m/z=308.2 (M−18+H)$^+$, 330.2 (M−18+Na)$^+$. $^1$H NMR (700 MHz, D$_2$O) δ 3.19-3.12 (m, 1H), 3.04 (ddd, J=13.3, 9.7, 5.7 Hz, 1H), 2.75 (s, 6H), 2.07-1.99 (m, 2H), 1.85-1.80 (m, 1H), 1.75-1.70 (m, 1H), 1.30-1.36 (m, 2H), 1.28-1.14 (m, 2H), 0.74 (t, J=7.6 Hz, 2H).

Example 12. (5-Amino-5-(ethoxycarbonyl)-7-(sulfamoylamino)heptyl)boronic acid hydrochloride

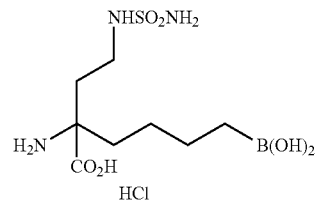

Step A. tert-Butyl 2-((tert-butoxycarbonyl)amino)-2-(2-((N-(tert-butoxycarbonyl)sulfamoyl)-amino)ethyl)-6-(4,4,5,5-tetramethyl-1,3,2-dioxaborolan-2-yl)hexanoate

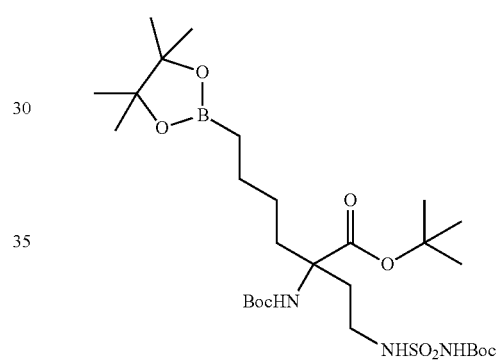

The mixture of tert-butyl 2-(2-aminoethyl)-2-((tert-butoxycarbonyl)amino)-6-(4,4,5,5-tetramethyl-1,3,2-dioxaborolan-2-yl)hexanoate (250 mg; 0.55 mmol), (tert-butoxycarbonyl)((4-(methyliminio)pyridin-1(4H)-yl)sulfonyl)amide (commercially available) (198 mg; 0.66 mmol), triethylamine (230 μL; 1.65 mmol) and DCM was stirred overnight. The reaction mixture was concentrated and the residue was purified by flash column chromatography, on silica gel (hexane/AcOEt, 20:1 to 5:1) to give 70 mg (20%) of the desired product as a white solid. ESI+MS: m/z=658.2 (M+Na)$^+$.

Step B. (5-Amino-5-(ethoxycarbonyl)-7-(sulfamoylamino)heptyl)boronic acid hydrochloride tert-butyl 2-((tert-butoxycarbonyl)amino)-2-(2-((N-(tert-butoxycarbonyl)sulfamoyl)amino)-ethyl)-6-(4,4,5,5-tetramethyl-1,3,2-dioxaborolan-2-yl)hexanoate (66 mg; 0.1 mmol) was treated with 4 M HCl in dioxane (1 mL). The mixture was stirred for 1 hour subsequent 2M HCl (aq) (1 mL) was added and stirring was continued for 1 hour. The reaction mixture was concentrated under reduced pressure ant the residue was purified by preparative HPLC (0.1-10% MeCN in water) to give a desired product (19 mg, 52%) as a colorless glass. ESI+MS: m/z=280.2 (M−18+H)$^+$, 302.2 (M−18+Na)$^+$. $^1$H NMR (700 MHz, D$_2$O) δ 3.20 (ddd, J=14.2, 8.2, 6.2 Hz, 1H), 3.16-3.09 (m, 1H), 2.20 (ddd, J=14.9, 8.1, 6.7 Hz, 1H), 2.16-2.08 (m, 1H), 1.90-1.95 (m, 1H), 1.88-1.78 (m, 1H), 1.44-1.30 (m, 3H), 1.24-1.11 (m, 1H), 0.80-0.65 (m, 2H).

Example 13. (5-Amino-5-(ethoxycarbonyl)-7-guanidinoheptyl)boronic acid dihydrochloride

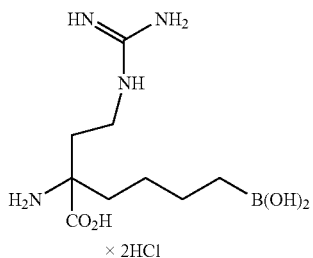

Step A. tert-Butyl 2-(2-(2,3-bis(tert-butoxycarbonyl)guanidino)ethyl)-2-((tert-butoxycarbonyl)-amino)-6-(4,4,5,5-tetramethyl-1,3,2-dioxaborolan-2-yl)hexanoate

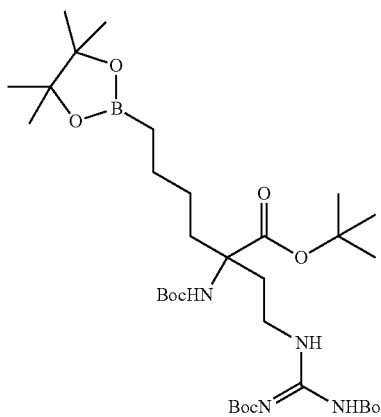

A mixture of tert-butyl 2-(2-aminoethyl)-2-((tert-butoxycarbonyl)amino)-6-(4,4,5,5-tetramethyl-1,3,2-dioxaborolan-2-yl)hexanoate (172 mg, 0.38 mmol), N,N'-bis(tert-butoxycarbonyl)-1H-pyrazole-1-carboxamidine (140 mg, 0.45 mmol) and acetonitrile (2 mL) was stirred at room temperature overnight. Then the solvent was evaporated under reduced pressure, the residue was dissolved in ethyl acetate (50 mL) and was washed with water (5 mL) and brine (10 mL), dried over $MgSO_4$, filtered and concentrated in vacuo to give a crude product. The crude material was purified by flash column chromatography, on silica gel (hexane/AcOEt 10:1) to give a desired product (121 mg, 46%) as a white solid. ESI+MS: m/z=700.0 (M+H)+.

Step B. (5-Amino-5-(ethoxycarbonyl)-7-guanidinoheptyl)boronic acid dihydrochloride tert-Butyl 2-(2-(2,3-bis(tert-butoxycarbonyl)guanidino)ethyl)-2-((tert-butoxycarbonyl)amino)-6-(4,4,5,5-tetramethyl-1,3,2-dioxaborolan-2-yl)hexanoate (100 mg; 0.14 mmol) was treated with 4 M HCl in dioxane (2 mL). The mixture was stirred for 1 hour subsequent 2M HCl (aq) (2 mL) was added and stirring was continued for 2 hours. The reaction mixture was concentrated under reduced pressure ant the residue was purified by preparative HPLC (0.1-10% MeCN in water) to give a desired product (15 mg, 32%) as a colorless glass. ESI+MS: m/z=247.1 (M−36+Na)+. $^1$H NMR (700 MHz, $D_2O$) δ 3.56 (t, J=6.5 Hz, 2H), 3.38 (ddd, J=14.3, 9.1, 5.4 Hz, 1H), 3.26 (ddd, J=14.1, 8.8, 6.8 Hz, 1H), 2.24 (ddd, J=15.8, 9.1, 6.8 Hz, 1H), 2.13 (ddd, J=14.6, 8.8, 5.4 Hz, 1H), 1.96 (ddd, J=14.5, 12.7, 4.5 Hz, 1H), 1.86 (ddd, J=14.6, 12.6, 4.6 Hz, 1H), 1.58-1.50 (m, 2H), 1.49-1.39 (m, 1H), 1.32-1.21 (m, 1H).

Example 14. 2-Amino-6-borono-2-(1-sulfamoylpiperidin-4-yl)hexanoic acid hydrochloride

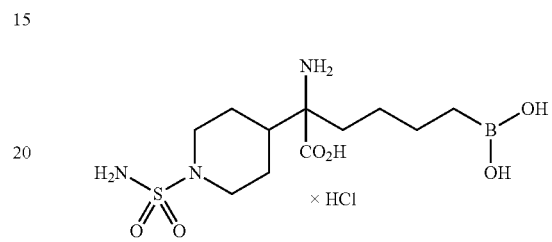

Step A. 2-Acetamido-N-(tert-butyl)-2-(piperidin-4-yl)-6-(4,4,5,5-tetramethyl-1,3,2-dioxa-borolan-2-yl)hexanamide hydrochloride

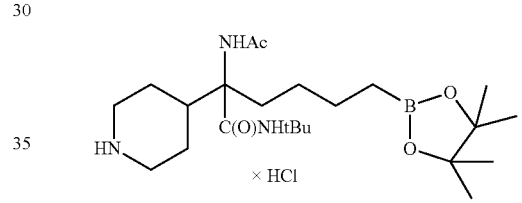

A mixture of tert-butyl 4-(2-acetamido-1-(tert-butylamino)-1-oxo-6-(4,4,5,5-tetramethyl-1,3,2-dioxaborolan-2-yl)hexan-2-yl)piperidine-1-carboxylate (3.51 g, 6.53 mmol) (Bioorganic & Medicinal Chemistry Letters, 2013, 23, 4837) and 4 N HCl in dioxane (16 mL) was stirred at room temperature for 65 hours. Then the solvent was evaporated under reduced pressure to give 3.10 g (100%) of the desired product as a yellow solid. ESI+MS: m/z=438.1 (M+1)+, 356.1 (M−Pin+1)+, ESI-MS: m/z=354.3 (M−Pin-1)−, $^1$H NMR (500 MHz, Chloroform-d) δ 8.27 (s, 1H), 3.70 (s, 9H), 2.13 (s, 2H), 1.46 (s, 4H), 1.39 (s, 8H), 1.24 (d, J=12.0 Hz, 3H), 1.21 (s, 13H), 0.73 (t, J=7.8 Hz, 2H).

Step B. tert-Butyl ((4-(2-acetamido-1-(tert-butylamino)-1-oxo-6-(4,4,5,5-tetramethyl-1,3,2-dioxaborolan-2-yl)hexan-2-yl)piperidin-1-yl)sulfonyl)carbamate

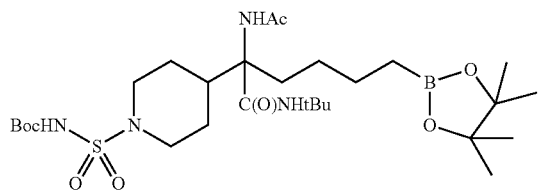

To a solution of chlorosulfonyl isocyanate (646 μL, 7.43 mmol) in dichloromethane (9 mL) was added dropwise a solution of tert-butanol (682 μL, 7.43 mmol) in DCM (4 mL) at 0° C. under argon. The solution was stirred at room temperature for 45 min. The solution of tert-butyl (chlorosulfonyl)carbamate (obtained as above) was added dropwise to a mixture of 2-acetamido-N-(tert-butyl)-2-(piperidin-4-yl)-6-(4,4,5,5-tetramethyl-1,3,2-dioxaborolan-2-yl)hexanamide hydrochloride (3.1 g, 6.75 mmol), triethylamine (3.01 mL, 21.60 mmol) and dichloromethane (45 mL) at 0° C. under argon. The reaction mixture was allowed to warm to RT and stirred at this temperature for 17 h. After this time the solution was diluted with dichloromethane (230 mL) and washed with $KHSO_4$ (1 M, aq) (90 mL) and water (45 mL). A organic layer was dried over $MgSO_4$ and concentrated. A crude product was purified by column chromatography on silica gel (hexane/AcOEt 2:3 to 1:5) to give (1.29 g, 31%) of tert-butyl ((4-(2-acetamido-1-(tert-butylamino)-1-oxo-6-(4,4,5,5-tetramethyl-1,3,2-dioxaborolan-2-yl)hexan-2-yl)piperidin-1-yl)-sulfonyl)carbamate as a white solid. ESI+MS: m/z=639.1 $(M+Na)^+$, ESI-MS: m/z=615.3 $(M-1)^-$, $^1H$ NMR (500 MHz, Chloroform-d) δ 6.98 (d, J=8.1 Hz, 2H), 3.92 (d, J=12.4 Hz, 1H), 3.83 (d, J=12.2 Hz, 1H), 2.94-2.85 (m, 1H), 2.84-2.72 (m, 2H), 2.36 (t, J=12.4 Hz, 1H), 1.99 (s, 3H), 1.81 (dd, J=22.7, 12.8 Hz, 2H), 1.48 (s, 9H), 1.45-1.43 (m, 1H), 1.42-1.48 (m, 2H), 1.36 (s, 9H), 1.22 (s, 12H), 1.09-0.94 (m, J, 1H), 0.95-0.79 (m, 1H), 0.74 (t, J=7.9 Hz, 2H).

Step C. 2-Amino-6-borono-2-(1-sulfamoylpiperidin-4-yl)hexanoic acid hydrochloride A mixture of tert-butyl ((4-(2-acetamido-1-(tert-butylamino)-1-oxo-6-(4,4,5,5-tetramethyl-1,3,2-dioxaborolan-2-yl)hexan-2-yl)piperidin-1-yl)sulfonyl)carbamate (150 mg, 2.43 mmol) and 3 N HCl (aq) (2.5 mL) was heated under reflux for 2 h. A solvent was evaporated under reduced pressure and the crude product was purified by preparative HPLC (0.1-15 MeCN in water) to give 2-amino-6-borono-2-(1-sulfamoylpiperidin-4-yl)hexanoic acid hydrochloride (54.8 mg, 60.1%) as a white solid. ESI+MS: m/z=320.2 $(M-18+1)^+$, ESI-MS=336.4 $(M-1)^-$, 318.3 $(M-18-1)^-$, $^1H$ NMR (500 MHz, Deuterium Oxide) 3.61-3.46 (m, 2H), 2.60-2.42 (m, 2H), 1.88-1.76 (m, 2H), 1.76-1.59 (m, 2H), 1.55-1.52 (m, 1H), 1.46-1.38 (m, 1H), 1.29-1.24 (m, 2H), 1.21-1.16 (m, 1H), 1.12-0.97 (m, 2H), 0.64 (t, J=7.28, 2H).

Example 15. 2-Amino-6-borono-2-(1-(N,N-dimethylsulfamoyl)piperidin-4-yl)hexanoic acid hydrochloride

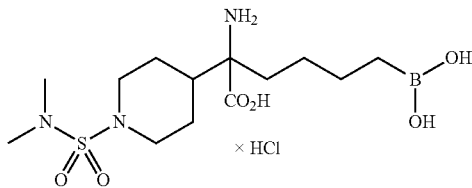 [SMILES: CN(C)S(=O)(=O)N1CCC(C(N)(CCCCB(O)O)C(=O)O)CC1]

Step A. 2-Acetamido-N-(tert-butyl)-2-(1-(N,N-dimethylsulfamoyl)piperidin-4-yl)-6-(4,4,5,5-tetramethyl-1,3,2-dioxaborolan-2-yl)hexanamide

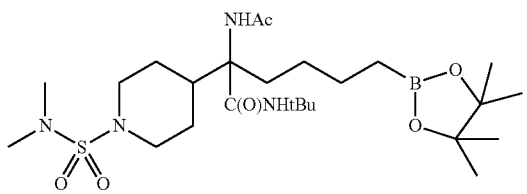

To a solution of 2-acetamido-N-(tert-butyl)-2-(piperidin-4-yl)-6-(4,4,5,5-tetramethyl-1,3,2-dioxaborolan-2-yl) hexanamide hydrochloride (422 mg, 0.89 mmol), triethylamine (397 μL, 2.85 mmol) in dichloromethane (8 mL) was added dropwise N,N-dimethylsulfamoyl chloride at 0° C., under argon. After stirring for 2 h at room temperature the mixture was diluted with DCM (50 mL) and washed with water (2×10 mL), dried over $MgSO_4$ and concentrated. The crude product was purified by flash chromatography, on silica gel (hexane/AcOEt 1:2 to 1:1) to give the desired product (158 mg, 33%) as a colorless oil. ESI+MS: m/z=545.1 $(M+1)^+$, 567.2 $(M+Na)^+$, ESI-MS: m/z 543.3 $(M-1)$, $^1H$ NMR (500 MHz, Chloroform-d) δ 6.99 (s, 1H), 5.47 (s, 1H), 3.74 (dd, J=33.7, 12.4 Hz, 2H), 2.79 (s, 6H), 2.75-2.68 (m, 1H), 2.32 (t, J=12.4 Hz, 1H), 2.00 (s, 3H), 1.76 (dd, J=28.5, 12.7 Hz, 2H), 1.36 (s, 9H), 1.28-1.25 (m, 5H), 1.24 (d, J=1.8 Hz, 3H), 1.22 (s, 11H), 0.74 (t, J=7.9 Hz, 2H).

Step B. 2-Amino-6-borono-2-(1-(N,N-dimethylsulfamoyl)piperidin-4-yl)hexanoic acid hydrochloride A mixture of 2-acetamido-N-(tert-butyl)-2-(1-(N,N-dimethylsulfamoyl)piperidin-4-yl)-6-(4,4,5,5-tetramethyl-1,3,2-dioxaborolan-2-yl)hexanamide (150 mg, 0.27 mmol) and 3 N HCl (aq) (2.5 mL) was heated under reflux for 2.5 h. After this time the reaction mixture was concentrated in vacuo and the residue was purified by preparative HPLC (5-20% MeCN in water) to give 2-amino-6-borono-2-(1-(N,N-dimethylsulfamoyl)piperidin-4-yl)hexanoic acid hydrochloride (47.3 mg, 44%) as a white solid. ESI+MS: m/z=348.2 $(M-18+1)^+$, ESI-MS: m/z=346.4 $(M-18-1)^-$, $^1H$ NMR (500 MHz, Deuterium Oxide) δ 3.67-3.53 (m, 2H), 2.76 (q, J=12.3 Hz, 2H), 2.67 (s, 6H), 1.95-1.74 (m, 2H), 1.73-1.61 (m, 2H), 1.49 (d, J=12.8 Hz, 1H), 1.44-1.35 (m, 1H), 1.29-1.15 (m, 4H), 1.10-1.00 (m, 1H), 0.64 (t, J=7.9 Hz, 2H).

Example 16. 2-Amino-6-borono-2-(1-(N-(4-(trifluoromethyl)benzyl)sulfamoyl)piperidin-4-yl)hexanoic acid hydrochloride

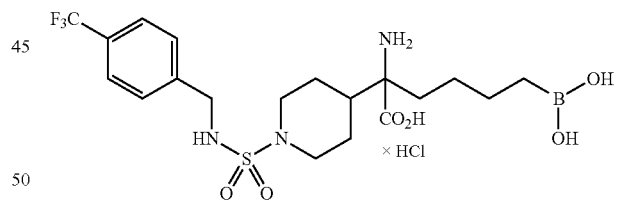

Step A. tert-Butyl ((4-(2-acetamido-1-(tert-butylamino)-1-oxo-6-(4,4,5,5-tetramethyl-1,3,2-dioxaborolan-2-yl)hexan-2-yl)piperidin-1-yl)sulfonyl)(4-(trifluoromethyl)benzyl)carbamate A solution of DIAD (134 µl, 0.68 mmol) in THF (1 mL) was added dropwise to a mixture of tert-butyl ((4-(2-acetamido-1-(tert-butylamino)-1-oxo-6-(4,4,5,5-tetramethyl-1,3,2-dioxaborolan-2-yl)hexan-2-yl)piperidin-1-yl)sulfonyl)carbamate (230 mg, 0.37 mmol), 4-trifluoromethyl)-benzyl alcohol (120 mg, 0.68 mmol) and triphenylphosphine (178 mg, 0.68 mmol) in THF (1 mL) at 0° C., under argon. The reaction mixture was allowed to warm to room temperature for 1.5 h and then stirred at ambient temperature for 3 days. The crude material was purified by flash chromatography on silica gel (AcOEt/hexane 1:5 to 1:2) to give tert-butyl ((4-(2-acetamido-1-(tert-butylamino)-1-oxo-6-(4,4,5,5-tetramethyl-1,3,2-dioxaborolan-2-yl)hexan-2-yl)piperidin-1-yl)sulfonyl)(4-(trifluoromethyl)benzyl)carbamate (143 mg, 49%) as a white solid. ESI+MS: m/z=797.2 (M+Na)$^+$, 775.2 (M+1)$^+$, ESI-MS: m/z=773.4 (M−1)$^−$. 1H NMR (500 MHz, Chloroform-d) δ 7.59 (d, J=8.1 Hz, 2H), 7.45 (d, J=8.0 Hz, 2H), 6.96 (s, 1H), 5.45 (s, 1H), 4.88 (s, 2H), 3.77 (d, 12.4 Hz, 1H), 3.67 (d, 12.3 Hz, 1H) 2.88-2.59 (m, 3H), 2.33 (t, J=12.3 Hz, 1H), 1.99 (s, 3H), 1.74 (dd, J=21.6, 12.8 Hz, 2H), 1.45 (s, 9H), 1.35 (s, 9H), 1.29-1.23 (m, 5H), 1.22 (s, 11H), 1.09-0.97 (m, 1H), 0.92-0.83 (m, 1H), 0.74 (s, 2H).

Step B. 2-Amino-6-borono-2-(1-(N-(4-(trifluoromethyl)benzyl)sulfamoyl)piperidin-4-yl)-hexanoic acid hydrochloride A mixture of ((4-(2-acetamido-1-(tert-butylamino)-1-oxo-6-(4,4,5,5-tetramethyl-1,3,2-dioxa-borolan-2-yl)hexan-2-yl)piperidin-1-yl)sulfonyl)(4-(trifluoromethyl)benzyl)carbamate (125 mg, 0.16 mmol) and 3 N HCl (aq) (2.5 mL) was heated under reflux for 3 h. Then the reaction mixture was concentrated under reduced pressure and the residue was purified by preparative HPLC (20-60% MeCN in water) to give 2-amino-6-borono-2-(1-(N-(4-(trifluoromethyl)-benzyl)sulfamoyl)piperidin-4-yl)hexanoic acid hydrochloride (15 mg, 18%) as a white solid. ESI+MS: m/z=478.0 (M−18+1)$^+$, ESI-MS: m/z=476.2 (M−18−1). 1H NMR (500 MHz, Methanol-d4) δ 7.63 (d, J=8.2 Hz, 2H), 7.54 (d, J=7.9 Hz, 2H), 4.24 (d, J=9.0 Hz, 2H), 3.75 (t, J=11.6 Hz, 2H), 2.68 (t, J=11.2 Hz, 2H), 2.06-1.97 (m, 1H), 1.97-1.75 (m, 4H), 1.64-1.60 (m, 2H), 1.44-1.34 (m, 2H), 1.27 (s, 1H), 0.80 (t, J=7.4 Hz, 1H), 0.64-0.59 (m, 1H), 0.55-0.49 (m, 1H).

Human Arginase Activity Assay

An enzymatic assay with recombinant human arginases 1 and 2 was used in order to establish inhibitory activity of the compounds. The assay was run in the 96-well plate format, each reaction in the total volume of 100 ul. The assay is based on urea measurement, which is a product of L-arginine enzymatic degradation. (Baggio et al. *J. Pharmacol. Exp. Ther.* 1999, 290, 1409-1416). The color product is developed by adding a mixture of reagent A (10 mM o-phthaldialdehyde and 0.4% polyoxyethylene (23) lauryl ether (w/v) in 1.8 M sulfuric acid) and reagent B (1.3 mM primaquine diphosphate, 0.4% polyoxyethylene (23) lauryl ether (w/v), and 130 mM boric acid in 3.6 M sulfuric acid) in equal proportions. The absorbance for each well was measured at 530 nm and was referred to the concentration curve determined using urea as a standard.

Briefly, to each well of a 96-well microtiter plate 40 µL of enzyme, 50 µL of the test compound solution, and 10 µL of enzyme substrate solution (L-arginine+manganese chloride) was added. For positive control, only the enzyme and substrate was added, the negative controls contained only manganese chloride. After incubating the microtiter plate at 37° C. for 60 min, 150 µL of a urea reagent was added to each well to stop the reaction. After quenching the reaction mixture, the plate was left for 20 min at room temperature in order to allow color development. Absorbance was measured with Envision® Reader (Perkin-Elmer) (λ=530 nm).

The IC$_{50}$ values were calculated using GraphPad Prism and divided into the following classes:

A:=1-100 nM; B=100-1000 nM; C=1-10 µM; D=10-100 µM; E>100 µM.

The inhibitory activity of the exemplary compounds according to the invention was classified as follows:

| Ex. No. | Structure | IUPAC Name | Activity Class |
|---|---|---|---|
| 1 | (structure: boronic acid chain with H$_2$N, CO$_2$H and sulfamoylamino-methyl group) | 2-Amino-6-borono-2-((sulfamoyl-amino)methyl)hexanoic acid | B* |
| 2 | (structure: boronic acid chain with H$_2$N, CO$_2$H and guanidinomethyl group) | 2-Amino-6-borono-2-(guanidinomethyl)hexanoic acid | A |
| 3 | (structure: boronic acid chain with H$_2$N, CO$_2$H and ureidomethyl group) | 2-Amino-6-borono-2-(ureidomethyl)hexanoic acid | D |

-continued

| Ex. No. | Structure | IUPAC Name | Activity Class |
|---|---|---|---|
| 4 | 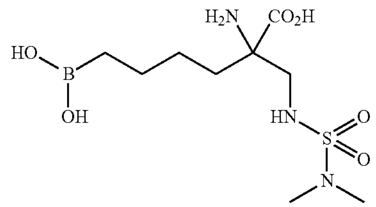 [SMILES: CN(C)S(=O)(=O)NCC(N)(CCCCB(O)O)C(=O)O] | 2-Amino-6-borono-2-(((N,N-dimethylsulfamoyl)amino)methyl)-hexanoic acid | B |
| 5 | 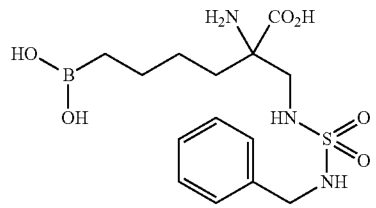 [SMILES: NC(CCCCB(O)O)(CNS(=O)(=O)NCc1ccccc1)C(=O)O] | 2-Amino-2-(((N-benzylsulfamoyl)-amino)methyl)-6-boronohexanoic acid | C |
| 6 | 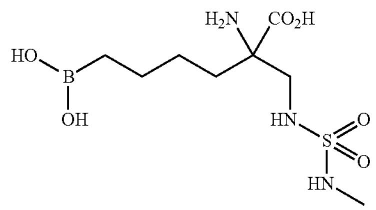 [SMILES: CNS(=O)(=O)NCC(N)(CCCCB(O)O)C(=O)O] | 2-Amino-6-borono-2(((N-methyl-sulfamoyl)amino)methyl)hexanoic acid | B |
| 7 | 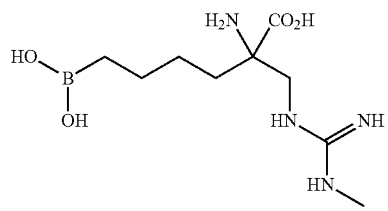 [SMILES: CNC(=N)NCC(N)(CCCCB(O)O)C(=O)O] | 2-Amino-6-borono-2-((3-methyl-guanidino)methyl)hexanoic acid | B |
| 8 | 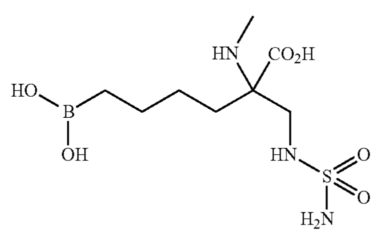 [SMILES: CNC(CCCCB(O)O)(CNS(N)(=O)=O)C(=O)O] | 6-Borono-2-(methylamino)-2-((sulfamoylamino)methyl)hexanomic acid | B |
| 9 | 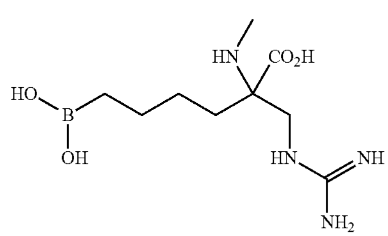 [SMILES: CNC(CCCCB(O)O)(CNC(=N)N)C(=O)O] | 6-Borono-2-(guanidinomethyl)-2-(methylamino)hexanoic acid | A |
| 10 | 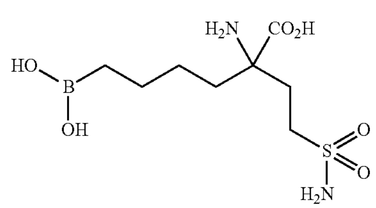 [SMILES: NC(CCCCB(O)O)(CCS(N)(=O)=O)C(=O)O] | 2-Amino-6-borono-2-(2-sulfamoyl-ethyl)hexanoic acid | C |

| Ex. No. | Structure | IUPAC Name | Activity Class |
|---|---|---|---|
| 11 | 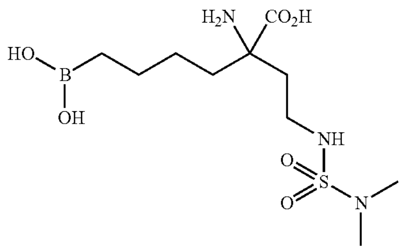 [SMILES: CN(C)S(=O)(=O)NCCC(N)(CCCCB(O)O)C(=O)O] | (5-Amino-7-((N,N-dimethyl-sulfamoyl)amino)-5-(ethoxycarbonyl)-heptyl)boronic acid | D |
| 12 | 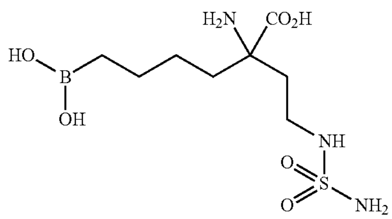 [SMILES: NC(CCCCB(O)O)(CCNS(N)(=O)=O)C(=O)O] | (5-Amino-5-(ethoxycarbonyl)-7-(sulfamoylamino)heptyl)boronic acid | C |
| 13 | 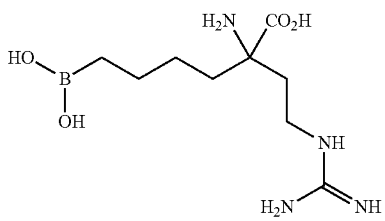 [SMILES: N=C(N)NCCC(N)(CCCCB(O)O)C(=O)O] | (5-Amino-5-(ethoxycarbonyl)-7-guanidinoheptyl)boronic acid | C |
| 14 | 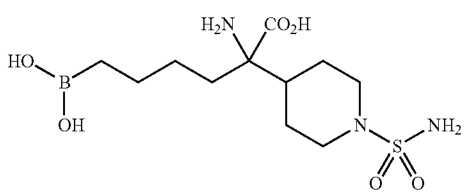 [SMILES: NC(CCCCB(O)O)(C(=O)O)C1CCN(S(N)(=O)=O)CC1] | 2-Amino-6-borono-2-(1-sulfamoyl-piperidin-4-yl)hexanoic acid | C |
| 15 | 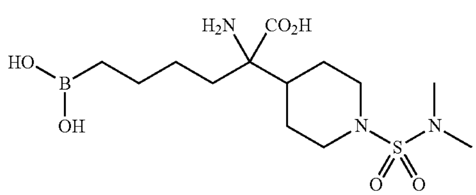 [SMILES: CN(C)S(=O)(=O)N1CCC(C(N)(CCCCB(O)O)C(=O)O)CC1] | 2-Amino-6-borono-2-(1-(N,N-dimethylsulfamoyl)piperidin-4-yl)hexanoic acid | D |
| 16 | 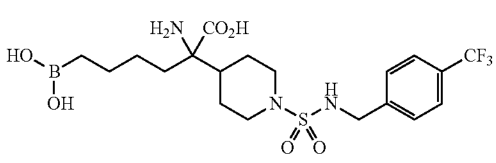 [SMILES: NC(CCCCB(O)O)(C(=O)O)C1CCN(S(=O)(=O)NCc2ccc(C(F)(F)F)cc2)CC1] | 2-Amino-6-borono-2-(1-(N-(4-(trifluoromethyl)benzyl)sulfamoyl)-piperidin-4-yl)hexanoic acid | C |

*The activity of the compound of Example 1 was initially estimated as belonging to class A, and later reassigned to class B.

INCORPORATION BY REFERENCE

All U.S. patents, U.S. published patent applications, and PCT published patent application designating the U.S. mentioned herein are hereby incorporated by reference in their entirety as if each individual publication or patent was specifically and individually indicated to be incorporated by reference. In case of conflict, the present application, including any definitions herein, will control.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by formula (I), or a stereoisomer, a tautomer, a pharmaceutically acceptable salt, or a solvate thereof:

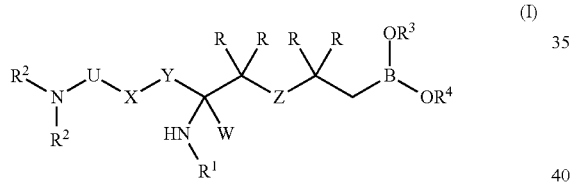

(I)

wherein:

U is —C(=NH)—, —S(O)—, or —S(O)$_2$—;

W is —CO$_2$H, —C(O)O((C$_1$-C$_6$)alkyl), —C(O)NHOH, —C(O)NHCN, —C(O)NH$_2$, —C(O)NH((C$_1$-C$_6$) alkyl), —C(O)NH((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)((C$_1$-C$_6$)alkyl), —S(O)$_2$NHC(O)((C$_1$-C$_6$)haloalkyl), —S(O)$_2$NHC(O) (aryl), —N(H)S(O)$_2$((C$_1$-C$_6$)alkyl), —N(H)S(O)$_2$ (aryl), N(H)S(O)$_2$((C$_1$-C$_6$)haloalkyl), —NHC(O)((C$_1$-C$_6$)alkyl), —NHC(O)((C$_1$-C$_6$)haloalkyl), —NHC(O) (aryl), —NHC(O)NH((C$_1$-C$_6$)alkyl), —NHC(O)NH (aryl), —C(O)N(H)S(O)$_2$((C$_1$-C$_6$)alkyl), —C(O)N(H) S(O)$_2$(aryl), —C(O)N(H)S(O)$_2$((C$_1$-C$_6$)haloalkyl), —P(O)(OH)$_2$, —CF$_3$,

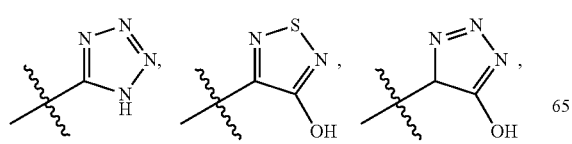

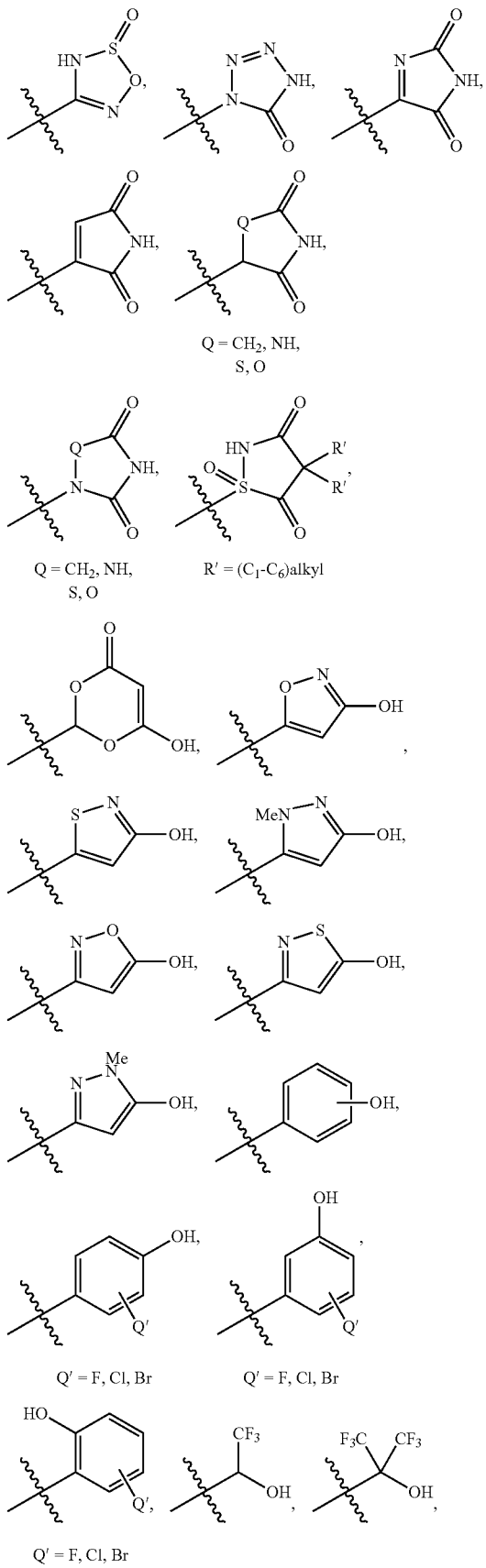

-continued

[structures with R' = (C₁-C₆)alkyl]

X is —N(R)₁— or —C(R)₂—;
Y is —(CR)₂—;
Z is —C(R)₂—, —O—, —S—, —SO—, or —SO₂—;
each R independently is selected from —H, —(C₁-C₃) alkyl, -halo, or —OH;
$R^1$ is —H or —SO₂NH₂ or —(C₁-C₃)alkyl;
each $R^2$ independently is selected from H, alkyl, aryl, arylalkyl, heteroaryl, heteroarylalkyl, heterocyclyl, or heterocyclylalkyl;
$R^3$ and $R^4$ are each independently selected from hydrogen, straight or branched (C₁-C₆)alkyl, and C(O)—R',
or $R^3$ and $R^4$ together with the boron atom to which they are bound via oxygen atoms form a 4-, 5-, 6-, or 7-membered ring that is fully saturated, or partially saturated.

2. A compound according to claim 1, wherein U is —C(=NH)—, or —S(O)₂—.
3. A compound according to claim 1, wherein each R is H.
4. A compound according to claim 1, wherein $R^1$ is H or CH₃.
5. A compound according to claim 1, wherein one of $R^2$ is H and the other is CH₃ or benzyl or para-(trifluoromethyl)benzyl.
6. A compound according to claim 1, wherein each $R^2$ is H.
7. A compound according to claim 1, wherein each $R^2$ is CH₃.
8. A compound according to claim 1, wherein $R^3$ is H.
9. A compound according to claim 1, wherein $R^4$ is H.
10. A compound according to claim 1, wherein W is —CO₂H or —C(O)NHOH.
11. A compound according to claim 1, wherein X is —NH— or —CH₂—.
12. A compound according to claim 1, wherein Y is —CH₂—.
13. A compound according to claim 1, wherein Z is —CH₂—.
14. A compound according to claim 1, wherein it is in racemic form.
15. A compound according to claim 1, which has the structural formula selected from the following formulae:

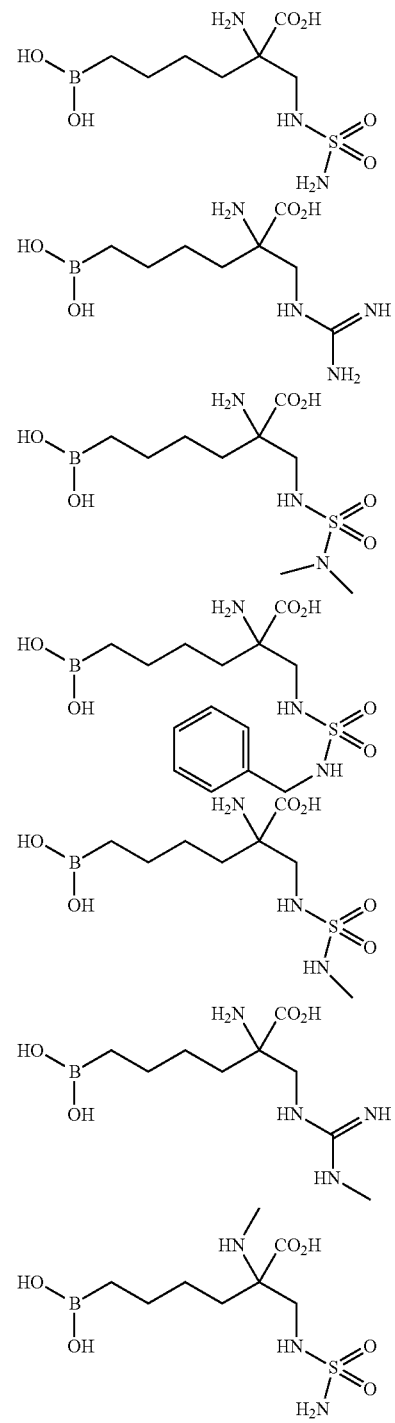

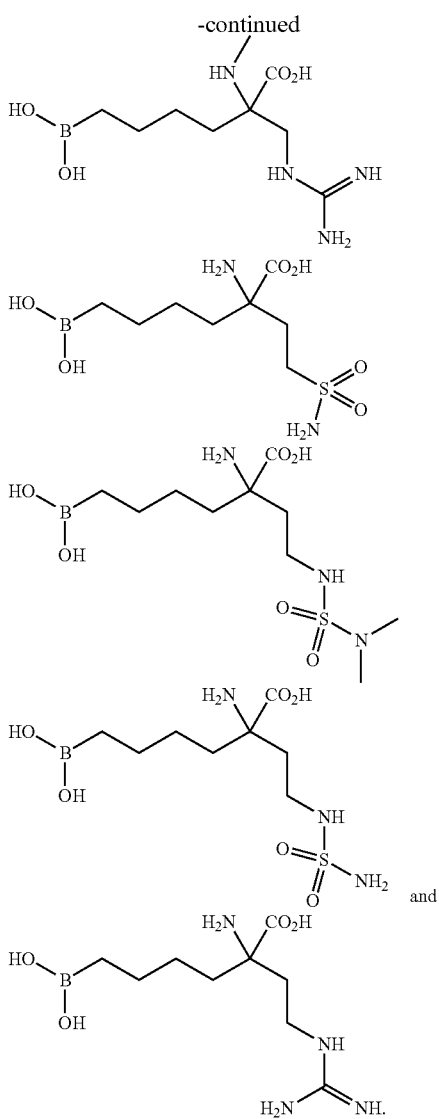

16. A compound according to claim 1, which is selected from:
2-amino-6-borono-2-((sulfamoylamino)methyl)hexanoic acid,
2-amino-6-borono-2-(guanidinomethyl)hexanoic acid, and
6-borono-2-(guanidinomethyl)-2-(methylamino)hexanoic acid,
or a stereoisomer, a tautomer, a pharmaceutically acceptable salt, and/or a solvate thereof.

17. A pharmaceutical composition comprising:
(i) a therapeutically effective amount of at least one compound according to claim 1, or a stereoisomer, tautomer, pharmaceutically acceptable salt, or solvate thereof; and
(ii) a pharmaceutically acceptable carrier.

18. A method for inhibiting arginase I, arginase II, or a combination thereof in a cell, comprising contacting the cell with at least one compound according to claim 1, or a stereoisomer, tautomer, pharmaceutically acceptable salt, or solvate thereof.

19. A method for the non-prophylactic treatment of a disease or condition associated with expression or activity of arginase I, arginase II, or a combination thereof in a subject, comprising administering to the subject therapeutically effective amount of at least one compound according to claim 1, or a stereoisomer, tautomer, pharmaceutically acceptable salt, or solvate thereof.

20. The method according to claim 19, wherein the disease or condition is selected from the group consisting of cardiovascular disorders, sexual disorders, wound healing disorders, gastrointestinal disorders, autoimmune disorders, immune disorders, infections, pulmonary disorders, hemolytic disorders, and cancers.

21. The method according to claim 20, wherein the disease or condition is cardiovascular disorder selected from the group consisting of systemic hypertension, pulmonary arterial hypertension (PAH), pulmonary arterial hypertension in high altitude, ischemia reperfusion (IR) injury, myocardial infarction, atherosclerosis.

22. The method according to claim 21, wherein the disease or condition is pulmonary arterial hypertension (PAH).

23. The method according to claim 21, wherein the disease or condition is myocardial infarction or atherosclerosis.

24. The method according to claim 20, wherein the disease or condition is a pulmonary disorder selected from the group consisting of chemically-induced lung fibrosis, idiopathic pulmonary fibrosis, cystic fibrosis, chronic obstructive pulmonary disease (COPD), and asthma.

25. The method according to claim 20, wherein the disease or condition is an autoimmune disorder selected from the group consisting of encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

26. The method according to claim 20, wherein the disease or condition is an immune disorder selected from the group consisting of myeloid-derived suppressor cell (MDSC) mediated T-cell dysfunction, human immunodeficiency virus (HIV), autoimmune encephalomyelitis, and ABO mismatch transfusion reaction.

27. The method according to claim 20, wherein the disease or condition is myeloid-derived suppressor cell (MDSC) mediated T-cell dysfunction.

28. The method according to claim 20, wherein the disease or condition is a hemolytic disorder selected from the group consisting of sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

29. The method according to claim 20, wherein the disease or condition is a gastrointestinal disorder selected from the group consisting of gastrointestinal motility disorders, gastric cancers, inflammatory bowel disease, Crohn's disease, ulcerative colitis, and gastric ulcers.

30. The method according to claim 20, wherein the disease or condition is a sexual disorder selected from the group consisting of Peyronie's disease and erectile dysfunction.

31. The method according to claim 20, wherein the disease or condition is ischemia reperfusion (IR) injury selected from the group consisting of selected from the group consisting of liver IR, kidney IR, and myocardial IR.

32. The method according to claim 20, wherein the disease or condition is a cancer selected from the group consisting of gastric, colon, breast, and lung cancers, including non-small cell lung carcinoma), renal cell carcinoma, prostate carcinoma, multiple myeloma, acute myeloid leukemia, neuroblastoma, glioblastoma, and melanoma.

33. The method according to claim 19, wherein the disease or condition is selected from the group consisting of renal disease inflammation, psoriasis, leishmaniasis, neurodegenerative diseases, wound healing, human immunodeficiency virus (HIV), hepatitis B virus (HBV), *Helicobacter pylori* infections, fibrotic disorders, arthritis, candidiasis, periodontal disease, keloids, adenotonsilar disease, African sleeping sickness and Chagas' disease.

34. The method according to claim 20, wherein the disease or condition is a wound healing disorder selected from the group consisting of infected and uninfected wound healing.

35. The method according to claim 19, wherein the subject is a mammal selected from the group consisting of human, dog, cat, horse, cow, pig, sheep, goat, and ape.

36. A method for providing organ protection during transport, comprising contacting an organ with a compound according to claim 1, or a stereoisomer, tautomer, pharmaceutically acceptable salt, or solvate thereof.

\* \* \* \* \*